United States Patent [19]

Gerlach et al.

[11] Patent Number: 5,405,844

[45] Date of Patent: Apr. 11, 1995

[54] TETRACYCLIC ANTIBIOTICS AND PROCESSES FOR THEIR PREPARATION

[75] Inventors: Uwe Gerlach; Rolf Hörlein; Norbert Krass, all of Frankfurt am Main; Rudolf Lattrell, Königstein/Taunus; Theo Wollmann; Michael Limbert, both of Hofheim am Taunus; Astrid Markus, Liederbach, all of Germany

[73] Assignee: Hoechst Aktiengesellschaft, Frankfurt am Main, Germany

[21] Appl. No.: 889,350

[22] Filed: May 28, 1992

[30] Foreign Application Priority Data

May 29, 1991 [DE] Germany ............ 41 17 564.6
Aug. 13, 1991 [DE] Germany ............ 41 26 653.6

[51] Int. Cl.$^6$ ............ C07D 477/00; A61K 31/40
[52] U.S. Cl. ............ 514/220; 540/302
[58] Field of Search ............ 540/302; 514/220

[56] References Cited

U.S. PATENT DOCUMENTS

| | | | |
|---|---|---|---|
| 4,772,683 | 9/1988 | Martel et al. | 540/200 |
| 4,841,042 | 6/1989 | Habich et al. | 540/200 |
| 4,841,043 | 6/1989 | Deziel et al. | 540/200 |

FOREIGN PATENT DOCUMENTS

| | | | |
|---|---|---|---|
| 0372582 | 6/1990 | European Pat. Off. | |
| 416953 | 3/1991 | European Pat. Off. | 540/302 |
| 422596 | 4/1991 | European Pat. Off. | 540/302 |
| 3509769 | 9/1986 | Germany . | |

OTHER PUBLICATIONS

R. N. Guthikonda, "Structure–Activity Relationships in the 2-Arylcarbapenem Series: Synthesis of 1-Methyl-2-arylcarbapenems", J. Med. Chem. 1987, 30, 871–880.

R. Deziel et al., "Synthesis of 1-62-Methylcarbapenem Key Intermediate Involving the Labile Acyl Auxiliary 4,4-dimethyl-1, 3-oxazolidine-2-thione", Tetrahedron Letters, vol. 30 (11) : 1345–1348 (1989).

*Primary Examiner*—Robert Gerstl
*Attorney, Agent, or Firm*—Finnegan, Henderson Farabow, Garrett & Dunner

[57] ABSTRACT

Tetracyclic antibiotics and processes for their preparation β-Lactam antibiotics of the formula I, and their pharmaceutically tolerable salts

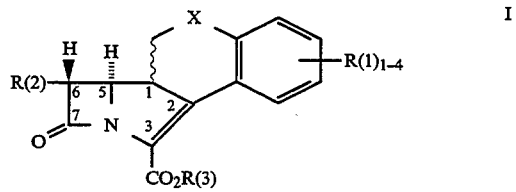

where
X is $(CH_2)_{0-2}$, $CR(a)R(b)$, O, $SO_{0-2}$ or $NR(c)$,
R1, R2 and R3 are a multiplicity of substituents, are outstanding antibiotics with remarkably good antibacterial activity both against gram-positive and against gram-negative microorganisms. They have a high stability to renal dehydropeptidase.

They are obtained by cyclization of the compounds II

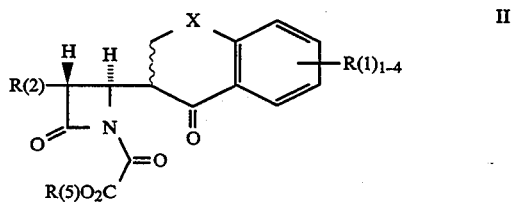

or III

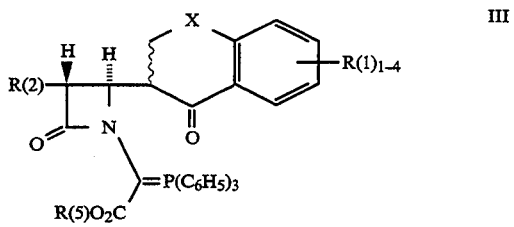

5 Claims, No Drawings

TETRACYCLIC ANTIBIOTICS AND PROCESSES FOR THEIR PREPARATION

The invention relates to β-lactam derivatives having a tetracyclic basic structure, which have a very high antimicrobial activity against gram-positive and gram-negative bacteria and are therefore suitable as pharmaceuticals for the treatment of microbial infections, and to processes for their preparation.

β-Lactams, such as, for example, penicillins, cephalosporins and carbapenems, are useful therapeutics for the treatment of bacterial infections. A disadvantage of most known antibiotics is that they are not active against all pathogens. Moreover, their frequent use leads to the occurrence of resistance. This makes the search for novel, highly active β-lactam structures necessary.

The invention therefore relates to a novel class of β-lactam antibiotics of the formula I, to their preparation and to their pharmaceutically tolerable salts

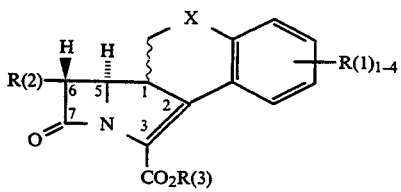

in which:

X is:

$(CH_2)_n$ where n=0, or 2;

CR(a)R(b), where R(a) and R(b) can be selected independently of one another from the following groups: H; $(C_1-C_6)$-alkyl; aryl and heteroaryl; [aryl is, for example, phenyl or naphthyl which is unsubstituted or substituted by $(C_1-C_4)$-alkyl, F, Cl, Br, $O(C_1-C_4)$-alkyl, OH, $OCO(C_1-C_4)$-alkyl, $NH_2$, $NH(C_1-C_4)$-alkyl, $OCOC_6H_5$ or $NHC_6H_5$, heteroaryl is a 5- to 6-membered ring which has 1 to 4 hetero atoms (for example N, O or S) and is unsubstituted or substituted by $(C_1-C_4)$-alkyl, F, Cl, Br, $O(C_1-C_4)$-alkyl, OH, $OCO(C_1-C_4)$-alkyl, $NH_2$, $NH(C_1-C_4)$-alkyl, $OCOC_6H_5$ or $NHC_6H_5$, such as, for example, furan, pyrrole, thiophene, thiazole, isothiazole, oxazole, isooxazole, pyrazole, imidazole, thiadiazole, triazole, tetrazole, pyridine, pyrimidine or pyridazine];

O;

$SO_n$ where n=0, or 2;

NR (c), where R (c) is selected from the group comprising H, $(C_1-C_6)$-alkyl, aryl, $CO(C_1-C_6)$-alkyl, CO-aryl, CO-heteroaryl, $(C_1-C_6)$-alkoxy-carbonyl, $(C_1-C_6)$-alkylsulfonyl and arylsulfonyl, R(1) is:

up to four substituents which are identical or different, selected from the group comprising H and $(C_1-C_6)$-alkyl, a substituent from the group comprising aryl, heteroaryl, OH, SH, $SOn(C_1-C_6)$-alkyl (where n=0, or 2), NR(b)R(c), (where R(b) and R(c) are as defined above), CN, $NO_2$, C(R(a))=NOR(b), (where R(a) and R(b) are as defined above), up to two substituents from the group comprising $CF_3$, F, Cl, Br, I, $O(C_1-C_6)$-alkyl, $OCO(C_1-C_6)$-alkyl, OCONR(d)R(e), (where R(d) and R(e) are selected independently of one another from the following groups: hydrogen and $(C_1-C_6)$-alkyl, and NR(d)R(e) can also correspond to a 5- or 6-membered ring system), $SO_2NR(d)R(e)$, (where R(d) and R(e) are as defined above), $CO(C_1-C_6)$-alkyl, COaryl, $CO_2H$, $CO_2(C_1-C_6)$-alkyl, CONR(d)R(e), (where R(d) and R(e) are as defined above), $CH_2R(f)$, (where R(f) is selected from the following groups: hydroxyl, $(C_1-C_6)$-alkoxy, acyloxy, aryloxy, heteroaryloxy, $(C_1-C_6)$-alkylthio, arylthio, heteroarylthio and the sulfinyl and sulfonyl compounds which can be derived therefrom, and NR(b)R(c), where R(b) and R(c) are as defined above. NR(b)R(c) can additionally be part of a cyclic or heterocyclic system); $NHCO(C_1-C_6)$-alkyl; $NHCOC_6H_5$ or NHCO-naphthyl; R(2) is:

H, $(C_1-C_4)$-alkyl, $CH_2OH$, $CH_2OCOR(a)$, $CH(OH)CH_3$, $CH(OCOR(a))CH_3$, $CH_2NR(b)R(c)$, $CH(NR(b)R(c))CH_3$, $C(CH_3)=NR(a)$, $CH[\oplus NR(g)R(h)R(i)]CH_3$, where R(a), R(b) and R(c) are as defined under R(1) and R(g), R(h) and R(i) are independent of one another and are $(C_1-C_6)$-alkyl groups; $NH_2$;

NHR(a)R(b); $NHCO(C_1-C_6)$-alkyl; $NHCOC_6H_5$ or NHCO-naphthyl;

R(3) is:

H, $(C_1-C_3)$-alkyl-OCO $(C_1-C_6)$-alkyl, $(C_1-C_3)$-alkyl-$OCO_2$ $(C_1-C_6)$-alkyl or (5-methyl-1,3-dioxolen-2-on-4-yl)methyl, and in which the preferred stereochemistry in position 5 is R and in position 6 is S.

Preferred compounds I are those in which R(1) is not hydrogen four times.

Preferred compounds I are those in which the substituents have the following meanings:

X is:

$CH_2$; $C(CH_3)_2$; CH-phenyl; O; $SO_n$ where n=0, 1 or 2; $NSO_2CH_3$; $NSO_2-C_6H_4-CH_3$; of which $CH_2$ and $SO_n$ where n=0, 1 or 2 are particularly preferred.

R(1) is:

H, $CH_3$, $C_6H_5$,

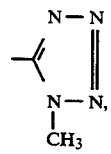

F, Cl, Br, $OCH_3$, OH, $OCOCH_3$, $OCONH-C_6H_5$, $NH_2$, $NHCOCH_3$, $NHSO_2CH_3$, $NHSO_2-C_6H_4-CH_3$, $NHCOCH_2NH_2$, CN, $COCH_3$, $C(CH_3=NOH$, $CO_2H$, $CO_2CH_3$, $CONH_2$, $CON(CH_3)_2$,

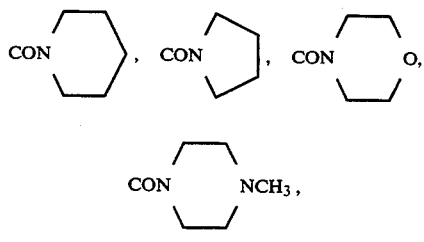

$CONHCH_2CO_2H$, $CH_2OCOCH_3$, $CH_2SCH_2CH_3$, $CH_2SCH_2CH_2NH_2$, $CH_2SCH_2CH_2NHCH(=NH)$, $CH_2SC_6H_5$,

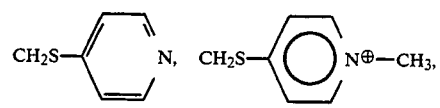

CH₂N(CH₃)₂, CH₂NHCOCH₂NH₂,

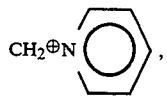

CH₂OH,

R(2) is:

H, CH₃, CH₂CH₃, CH₂OH, CH(OH)CH₃, CH(O-COCH₃)CH₃, CH(OCOCH₂-C₆H₅)CH₃, CH(OCOCH₂O-C₆H₅)CH₃, CH(NH₂)CH₃, CH[N⊕(CH₃)₃]CH₃, CH(NHCOCH₃)CH₃, CH(NHSO₂CH₃)CH₃, CH(NHSO₂C₆H₅)CH₃, CH(NHCOCH₂NH₂)CH₃, of which CH(OH)CH₃ having the R-configuration is particularaly preferred, R(3) is:

H, CH₂OCOCH₃, CH₂OCOCH₂CH₃, CH₂OCOCH₂CH₂CH₃, CH₂OCOCH(CH₃)₂, CH₂OCOC(CH₃)₃, CH₂OCOC(CH₃)₂CH₂CH₃, CH(CH₃)OCOCH₃, CH(CH₂CH₃)OCOCH₃, CH(CH₃)OCOC(CH₃)₃, CH(CH₃)OCO₂CH₃, CH(CH₃)OCO₂CH₂CH₃, CH(CH₃)OCO₂CH(CH₃)₂, CH₂OCO₂CH₃.

Particularly preferred compounds are those in which the CH₂X group is in the β-position, i.e. trans to the C(5) hydrogen.

The invention furthermore includes processes for the preparation of compounds of the formula I and their pharmaceutically tolerable salts, which comprise a) preparing a compound of the formula II

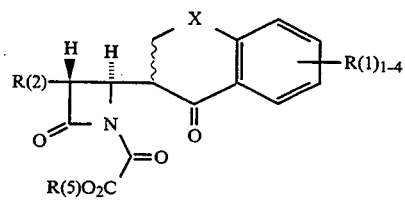

in which R(1), R(2) and X are as defined above, NH and OH groups are substituted by protective groups if necessary and R(5) is a carboxyl protective group, cyclizing the compounds of the formula II with alkane-phosphonous acid esters or trialkyl phosphites, removing the protective groups and, if necessary, converting the products obtained into pharmaceutically tolerable salts, or b) preparing a compound of the formula III

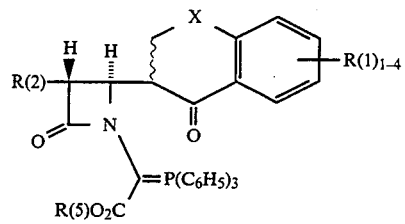

in which R(1), R(2) and X are as defined above, NH and OH groups are substituted by protective groups if necessary, and R(5) is a carboxyl protective group or one of the groups listed under R(3), cyclizing the compounds of the formula III by heating, if necessary removing the protective groups and, if necessary, converting the products I obtained into pharmaceutically tolerable salts, or c) converting the compounds of the formula I, in which R(3) is a hydrogen, obtained by process variants a) and b) into the esters having the groups given under R(3).

The preparation of compounds of the formula I by process a) is shown in scheme 1.

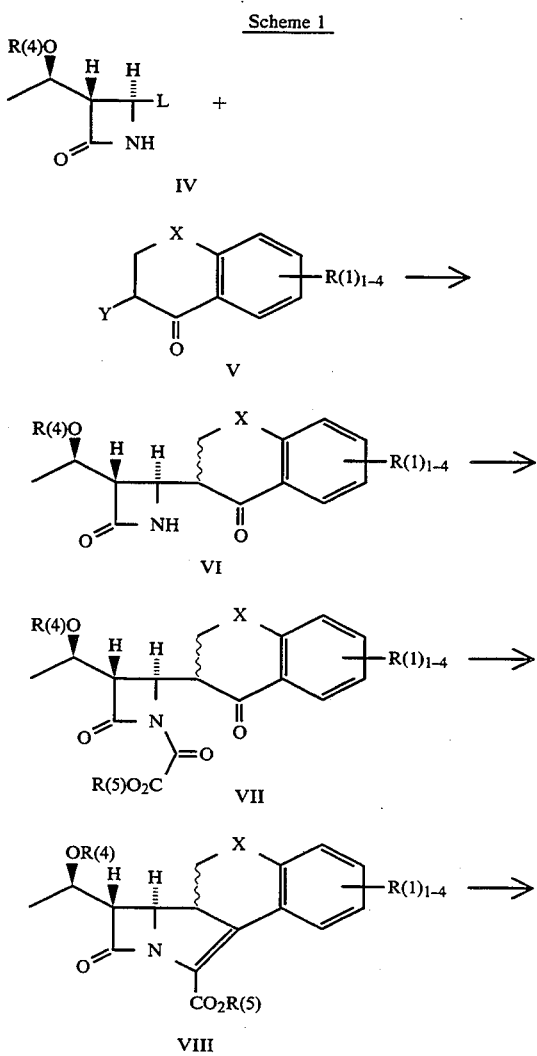

-continued
Scheme 1

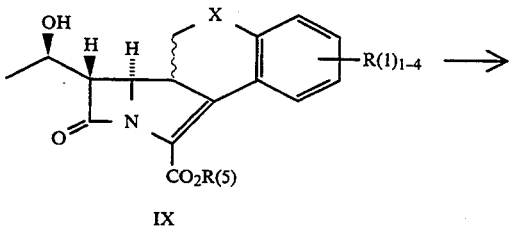

IX

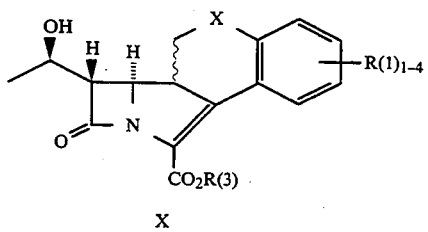

X

Starting from compounds of the formulae IV and V, compounds of the formula VI are first prepared. In this case, X and R(1) are as defined above, L is a leaving group, for example —Cl or —OCOCH$_3$. R(4) is an alcohol protective group such as the trimethylsilyl group or the tetrahydropyranyl group, which can be cleaved, for example, by acid hydrolysis, or the tert-butyldimethylsilyl group or the triethylsilyl group, which can be cleaved, for example, by tetrabutylammonium fluoride, or the benzyloxycarbonyl group or the 4-nitrobenzyloxycarbonyl group, which can be cleaved by hydrogenolysis, or alternatively the allyloxycarbonyl group, which can be cleaved by Pd[P(C$_6$H$_5$)$_3$]$_4$. Y can be hydrogen or alternatively bromine.

The reactions are carried out by converting compounds of the formula V into the metal enolates analogously to literature processes, where, inter alia, the following metals can be employed in the oxidation states indicated: Li(+1), Na(+1), K(+1), Mg(+2), B(+3), Si(+4), Sn(+2), Zn(+2) and Ti(+4). The metal enolates can then be reacted with compounds of the formula IV or alternatively generated in their presence. If necessary, Lewis acids such as, for example, trimethylsilyl triflates, zinc(II) chloride or alternatively titanium(IV) chloride must be added to the reaction. Reaction conditions are chosen such as those which have been described in the literature, for example U.S. Pat. No. 4,841,043, U.S. Pat. No. 4,772,683, German Offenlegungsschrift DE 3,509,769 A1 and Deziel et al., Tetrahedron Letters 30 (11) (1989), 1345-1348.

The compounds of the formula VI can be formed as mixtures of the α- and β-isomer. Depending on the conditions and starting material used, the ratio α/β is between 9:1 and 1.5. The diastereomers can be separated by chromatography or alternatively crystallization. However, mixtures can also be further reacted and separated in later stages.

Acylation to give compounds of the formula VII is carried out analogously to literature processes in a manner known per se. R(5) is a carboxyl protective group such as, for example, the benzyl group, the 4-nitrobenzyl group or alternatively the allyl or the 2-chloroallyl group. These can later be cleaved by hydrogenolysis or using Pd[P(C$_6$H$_5$)$_3$]$_4$.

Cyclization to give compounds of the formula VIII is carried out using 2-10 equivalents of alkanephosphonous acid esters or trialkyl phosphites, preferably using 3-5 equivalents of dimethyl methanephosphonite or diethyl methanephosphonite. The reaction is carried out at temperatures from 60° C. to 200° C., preferably from 110° C. to 170° C. in an inert aprotic solvent. Suitable solvents are, for example, toluene, xylene or alternatively mesitylene. The reaction time depends on the reactants, the temperature and the solvent and is between 5 minutes and 48 hours. The products are purified by chromatography or crystallization after the removal of the solvent.

The removal of the protective groups to give compounds of the formula IX and further to give compounds of the formula X in which R(3) is hydrogen is dependent on the protective groups selected and is carried out as described above in analogy to general literature methods. The compounds of the formula X can be purified by chromatography on RP-18 silica gel or by crystallization.

Scheme II

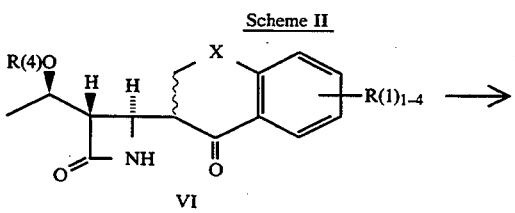

VI

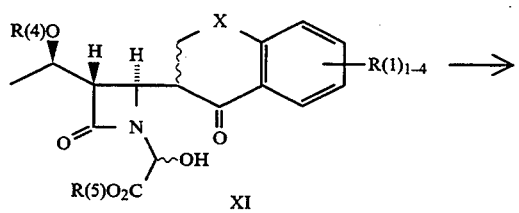

XI

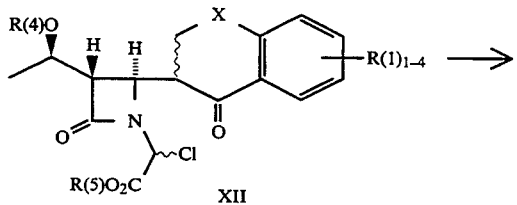

XII

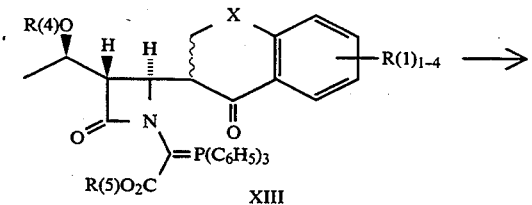

XIII

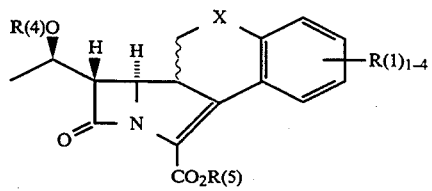

VIII

The compounds of the formula I are also accessible by process b), which is shown in scheme II.

Compounds of the formula XIII are prepared starting from compounds of the formula VI analogously to described literature methods, such as R.N. Guthikonda et al., J. Med. Chem. 30 (1987), 871–880.

Cyclization of compounds XIII to give compounds of the formula VIII is carried out in inert aprotic solvents, such as, for example, toluene, xylene or mesitylene. The reaction is carried out at temperatures from 60° C. to 200° C. preferably from 110° C. to 170° C. The reaction time depends on the reactants, the temperature and the solvent and is between 5 minutes and 48 hours. The products are purified by chromatography and crystallization after the removal of the solvent, the protective groups are then removed as described in process a) and, if necessary, pharmaceutically tolerable salts are prepared.

R(5) can in this case also be one of the ester components listed under R(3), so that after removal of the alcohol protective group esters of the formula (1) (R(3) is not H) which can be cleaved in vivo are obtained directly.

Compounds having the formula XV in which R(6) is alkyl, aryl or heteroaryl can be prepared by acylation of compounds of the formula IX according to literature procedures and subsequent removal of the carboxyl protective group.

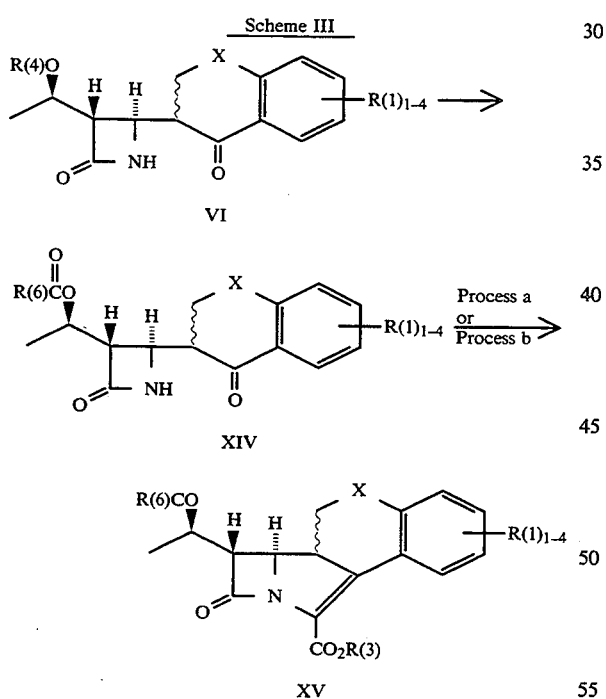

The compounds of the formula VI in which R(4) is the trimethylsilyl group, the triethylsilyl group or the tert-butyldimethylsilyl group can furthermore be converted, as shown in scheme III, into compounds of the formula XIV by processes known per se using Lewis acids such as iron(III) chloride and acid anhydrides and these can then be converted into the product having the formula XV by process a) or b).

The aminoethyl derivatives of the formula XVIII in scheme IV, in which R(7) is an amino protective group, such as, for example, allyloxycarbonyl or 4-nitrobenzyloxycarbonyl, are obtained as follows: starting from the compounds of the formula VI described above, the alcohol of the formula XVI is prepared. If, for example, R(4) is a tert-butyldimethylsilyl group, compounds of the formula XVI are obtained by reactions with mineral acids, such as, for example, hydrochloric acid in methanol, or Lewis acids, such as, for example, boron trifluoride in acetonitrile.

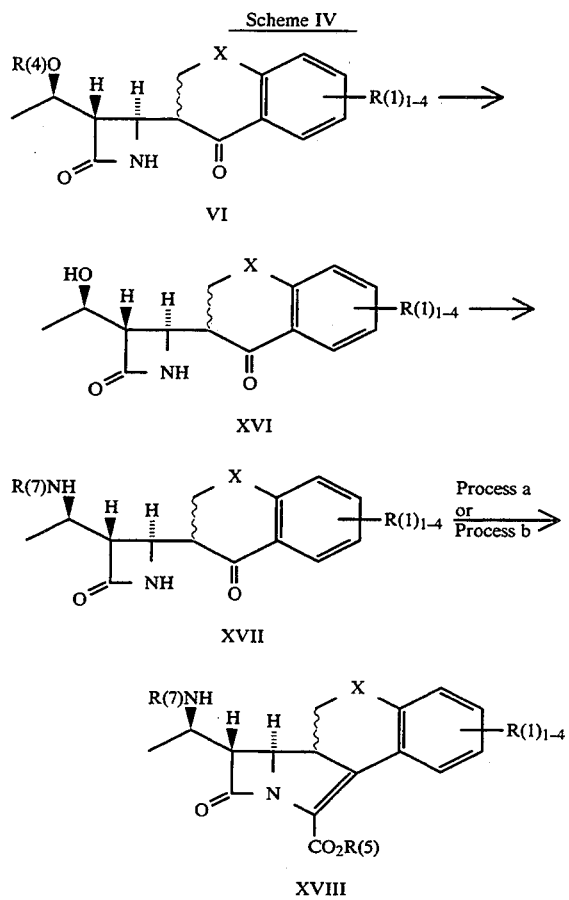

Compounds of the formula XVII are obtained by methods such as are described, for example, in European Offenlegungsschrift 89122711.8, and subsequent protection of the amino group, for example with the allyloxycarbonyl group, and are converted into compounds of the formula XVIII by process a) or b).

After removal of the amino protective group, derivatizations, for example acylation or alkylation, can be carried out by literature methods, before the carboxyl protective group is subsequently cleaved.

The substituents R(1) are introduced into the compounds of the formula I by means of the precursors of the formula V. However, in some cases it is advantageous to introduce the substituents R(1) into compounds having the formula VIII by reactions known per se, for example by following conversions: R(1)=CH$_2$OH to

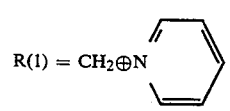

or R(1)=CO$_2$C$_6$F$_5$ to R(1)=CON(CH$_3$)$_2$. The removal of the protective groups is then carried out as described above.

If it is intended to obtain compounds of the formula I in which R(3) is (C$_1$-C$_6$)-alkanoyloxy-(C$_1$-C$_3$)-alkyl, (C$_1$-C$_6$)-alkoxycarbonyloxy-(C$_1$-C$_6$)-alkyl or (2-oxo-5-methyl-1,3-dioxolen-4-yl)methyl by process c), the compounds of the formula I in which R(3) is hydrogen are reacted with a compound of the formula XIX or XX

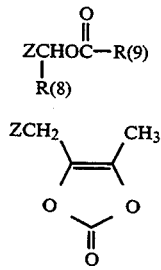

in a manner known per se.

R(8) in this case is hydrogen or a (C$_1$-C$_2$)-alkyl group, R(9) is a (C$_1$-C$_6$)-alkyl group or a (C$_1$-C$_6$)-alkoxy group and Z is halogen, preferably chlorine, bromine or iodine. Processes which are known for esterification reactions are used here.

Examples of pharmaceutically tolerable salts of the compounds of the formula I which may be mentioned are lithium, sodium, potassium, calcium and magnesium salts or salts with organic amines such as diethylamine, benethamine, piperazine or tromethamine.

The compounds of the formula I according to the invention and their pharmaceutically tolerable salts exhibit remarkably good antibacterial activity both against gram-positive and gram-negative microorganisms. The compounds have a high stability to renal dehydropeptidase.

The compounds of the formula I are also unexpectedly highly active against penicillinase- and cephalosporinase-forming bacteria. As they additionally exhibit favorable toxicological and pharmacological properties, they are useful chemotherapeutics.

The invention also relates to pharmaceutical preparations for the treatment of microbial infections, which preparations contain one or more of the compounds according to the invention.

The products according to the invention can also be used in combinations with other active substances, for example from the penicillin, cephalosporin, quinolone, glycopeptide or aminoglycoside series.

The compounds of the formula I and their pharmaceutically tolerable salts can be administered orally, intramuscularly or intravenously.

Pharmaceutical preparations which contain one or more compounds of the formula I as the active substance can be prepared by mixing the compounds of the formula I with a plurality of pharmacologically tolerable excipients or diluents, such as fillers, emulsifiers, lubricants, flavor correctants, colorants or buffer substances and bringing into a suitable pharmaceutical preparation form, such as tablets, coated tablets, capsules or a suspension or solution suitable for parenteral administration.

Examples of excipients or diluents which may be mentioned are: tragacanth, lactose, talc, agar-agar, polyglycols, ethanol and water. Buffer substances are, for example, organic compounds, such as, for example, N,N'-dibenzylethylenediamine, diethanolamine, ethylenediamine, N-methylglucamine, N-benzylphenethylamine, diethylamine and tris(hydroxymethyl)aminomethane (tromethamine), or inorganic compounds, such as phosphate buffer, sodium bicarbonate and sodium carbonate. Suspensions or solutions in water with or without buffer substances are preferably suitable for parenteral administration. It is also possible to administer the active substances as such in a suitable form, for example in capsules, without excipients or diluents.

Suitable doses of the compounds of the formula I or their pharmaceutically tolerable salts are from about 0.4 g to a maximum of about 20 g per day, preferably from 1 to 10 g, in particular 2 to 6 g/day for an adult of about 75 kg body weight.

Individual or, in general, multiple doses can be administered, where the individual dose can contain the active substance in an amount from about 50 to 1,000 mg, preferably from about 100 to 500 mg.

The following exemplary embodiments of 5R,6S-compounds which can be prepared according to the invention serve to illustrate the invention further.

The following abbreviations have been used in the examples: THF=tetrahydrofuran, DMF=dimethylformamide, s=singlet, d=doublet, t=triplet, q=quartet, m=multiplet, mc=centered multiplet, bs=broad singlet.

EXAMPLE 1

Potassium (1S,5R,6S)-6-[(1R)-1-hydroxyethyl]-(1,2,3,4-tetrahydronaphtho)[2,1-a]carbapen-2-em-3-carboxylate.

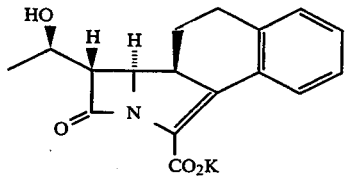

Step 1:

(3S,4R)-3-[(1R)-1-tert-Butyldimethylsilyloxyethyl]-4-[(2R)-1-oxo-1,2,3,4-tetrahydronaphth-2-yl]azetidin-2-one and 3.0 g (11.8 mmol) of iodine were added at room temperature to a suspension of 126 g (1,06 mol) of tin powder in 260 ml of DMF and 130 ml of methylene chloride. After complete decolorization of the solution, 4.2 g (21.6 mmol) of silver tetrafluoroborate were added and the mixture was stirred at room temperature for 15 min. The mixture was cooled to 10° C. and a solution of 120 g (0.53 mol) of 2-bromotetralone in 60 m.1 of DMF and 30 ml of methylene chloride was added dropwise in the course of 1.5 h, the internal temperature being kept at 10° C.±2° C. After a further 60 min at room temperature, the reaction solution was poured into 1.5 l of a mixture of cyclohexane/ethyl acetate (1:1) and filtered through kieselguhr (®Celite). The organic phase was extracted with 300 ml of 1N HCl, 600 ml of 5% strength sodium hydroxide solution and 300 ml of water and dried over MgSO$_4$. According to HPLC, the crude product contained the two isomers in the ratio α/β=2:3. It was possible to isolate 26.3 g (20%) of the β-isomer (purity>97%) by recrystallization from n-heptane. —$^1$H-NMR (270 MHz, CDCl$_3$):δ=0.10 (s, 6H, SiCH$_3$); 0.87 (s, 9H, SiC(CH$_3$)$_3$); 1.28 (d, 3H, CH—CH$_3$); 2.08 and 2.30 (2×mc, 2×1H, CH$_2$—CH$_2$—CH); 3.07-3.14 (m, 3 H, CH$_2$—CH$_2$—CH and H-3); 4.25 (mc, 1H, CH—CH$_3$); 4.45 (dd, 1 H, H-4); 5.77 (bs, 1H, NH); 7.25-7.38 (m, 2H, aromatic H); 7.52 (mc, 1 H, aromatic H); 8.02 (d, 1 H, aromatic H).

Step 2:

Allyl [(3S,4R)-3-[(1R)-1-tert-butyldimethylsilyloxyethyl]-4-[(2R )-1-oxo-1,2,3,4-tetrahydronaphth-2-yl)]-2-oxoazetidin- 1-yl ]-2-oxoacetate.

1.07 g (10.7 mmol) of CaCO$_3$ and 1.59 g (10.7 mmol) of allyl oxalyl chloride were added at 0° C. under argon as protective gas to a solution of 2.0 g (5.35 mmol) of (3S,4R)-3-[(1R)-1-tert-butyldimethylsilyloxyethyl]-4-[2R)-1-oxo-1,2,3,4-tetrahydronaphth-2-yl]azetidin-2-one in 45 ml of anhydrous methylene chloride. 1.81 ml (1.34 g, 10.4 mmol) of ethyldii. sopropylamine in 10 ml of methylene chloride were added dropwise to the mixture in the course of 1 h and it was stirred for a further 2 h at the given temperature. The solid was filtered off with suction and the organic phase was extracted twice with 20 ml of water each time. After drying over MgSO4, the solvent was removed on a rotary evaporator and the residue was chromatographed (eluent: toluene/ethyl acetate=30:1) on silica gel (deactivated with 10% H$_2$O). Yield: 1.95 g (75%), white crystals. — $^1$H-NMR (270 MHz, CDCl$_3$): δ=0.06 and 0.08 (2×s, 2×3 H, SiCH$_3$); 0.85 (s, 9H, SiC(CH$_3$)$_3$); 1.19 (d, 3H, CH—CH$_3$, J=6 Hz), 2.03 and 2.27 (2×mc, 2×1H, CH$_2$—CH$_2$—CH); 3.12 (dd, 2H, CH$_2$—CH$_2$—CH, J=4.9 Hz); 3.21 (mc, 1 H, CH$_2$—CH—CH$_2$, J=4.5, 10 Hz); 3.32 (dd, 1H, H-3, J=4 Hz); 4.33 (mc, 1H, CH—CH$_3$); 4.67 (dd, 1H, H-4, J=4 Hz); 4.81 (mc, 2H, CH$_2$—CH=CH$_2$); 5.27–5.45 (m, 2H, CH$_2$—CH=CH$_2$, J=10, 17 Hz, J(allyl)=1Hz); 5.97 (mc, 1H, CH$_2$—CH=CH$_2$); 7.23-7.37 (m, 2H, aromatic H); 7.50 (m, 1H, aromatic H); 8.04 (d, 1H, aromatic H).

Step 3:

Allyl (1S,5R,6S)-6-[(1R)-1-tert-butyldimethylsilyloxyethyl ]-(1,2,3,4-tetrahydronaphtho)[2,1-a]carbapen-2-em-3-carboxylate.

300 mg (0.62 mmol) of allyl [(3S,4R)-3-[(1R)-1-tert-butyldimethylsilyloxyethyl ]-4- [(2R)-1-oxo-1,2,3,4-tetra-hydronaphth-2-yl ]-2-oxoazetidin-l-yl]-2-oxoacetate and 255 mg ( 2.12 mmol ) of diethyl methanephosphonite were stirred at 160° C. for 3 h in 10 ml of anhydrous mesitylene under argon. After removal of the solvent in a high vacuum and after column chromatography ( silica gel, eluent: toluene/ethyl acetate=30:1), 176 mg (63%) of the cyclized product, m.p 126° C., were obtained. — $^1$H-NMR (270 MHz, CDCl$_3$): δ=0.11 (s, 6H, SiCH$_3$); 0.92 (s, 9H, SiC(CH$_3$)$_3$); 1.27 (d, 3H, CH—CH$_3$); 1.94 and 2.08 (2×mc, 2×1H, CH$_2$—CH$_2$—CH); 3.07 ( dd, 2H, CH$_2$—CH$_2$—CH); 3.18 (mc, 1H, CH$_2$—CH$_2$—CH); 3.28 (dd, 1H, H-6); 4.20-4.35 (m, 2H, CH—CH$_3$ and H-5); 4.78 (mc, 2H, CH$_2$—CH=CH$_2$); 5.23-5.47 (m, 2H, CH$_2$—CH=CH$_2$); 5.98 (mc, 1H, CH$_2$—CH=CH$_2$); 7.10-7.25 (m, 3H, aromatic H); 7.77 (d, 1H, aromatic H).

Step 4:

Allyl (1S,5R,6S)-6-[(1R)-1-hydroxyethyl]-(1,2,3,4-tetrahydronaphtho)[2,1-a ]carbapen-2-em-3-carboxylate.

465 mg (7.75 mmol) of acetic acid (10% strength solution in THF) were added at 0° C. to a solution of 586 mg (1.29 mmol) of allyl (1S,5R,6S)-6-[(1R)-1-tert-butyl-dimethylsilyloxyethyl](1,2,3,4-tetrahydronaphtho)[2,1a]carbapen-2-em-3-carboxylate in 6 ml of anhydrous THF and a solution of 1.22 g (3.87 mmol) of tetrabutylammonium fluoride trihydrate in 11 ml of THF was then added dropwise in the course of 15 min. The ice-cooling was removed and the reaction mixture was stirred at room temperature for a further 54 h. The solvent was removed in vacuo, the residue was taken up in ethyl acetate and the organic phase was extracted with 25 ml each of a satd. NaHCO$_3$ solution and water. After drying over MgSO$_4$ and concentrating the solution, the product was isolated by chromatography on silica gel (eluent: toluene/ethyl acetate=3:1). Yield: 216 mg (49%). — $^1$H—NMR (270 MHz, CDCl$_3$): δ=1.37 (d, 3H, CH—CH$_3$); 1.85-1.99 (m, 2H, CH$_2$—CH$_2$CH and OH); 2.08–2.20 (m, 1H, CH$_2$—CH$_2$—CH); 3.06 (dd, 2H, CH$_2$—CH$_2$—CH); 3.22 (mc, 1H, CH$_2$—CH$_2$—CH); 3.32 (dd, 1H, H-6); 4.23-4.38 (m, 1H, CH—CH$_3$); 4.35 (dd, 1H, H-5); 4.78 (mc, 1H, CH$_2$—CH=CH$_2$); 5.24-5.48 (m, 2H, CH$_2$—CH=CH$_2$); 5.98 (mc, 1H, CH$_2$—CH=CH$_2$); 7.10-7.29 (m, 3H, aromatic H), 7.78 (d, 1H, aromatic H).

Step 5:

Potassium (1S,5R,6S)-6-[(1R)-1-hydroxyethyl]-(1,2,3,4tetrahydronaphtho)[2,1-a]carbapen-2-em-3-carboxylate.

A solution of 185 mg (1.0 mmol) of potassium 2-ethylhexanoate in 2 ml of ethyl acetate was added with exclusion of oxygen to 309 mg (0.92 mmol) of allyl (1S,5R,6S)-6-[(1R)-1-hydroxyethyl]-(1,2,3,4-tetrahydronaphtho)[2,1-a]carbapen-2-em-3-carboxylate, dissolved in 3 ml of methylene chloride. After addition of 12 mg (0.05 mmol) of triphenylphosphine and 30 mg (0.03 mmol) of Pd[P(C$_6$H$_5$)$_3$]$_4$, the mixture was stirred at room temperature for 30 min and diluted with 15 ml of methylene chloride, and 20 ml of water were added. The water phase was separated off and the methylene chloride was again extracted with 20 ml of water. The combined water phases were then extracted with 15 ml of methylene chloride and freeze-dried. The residue was chromatographed on ®LiChroprep RP18 using water. After freeze-drying the product-containing fractions, 155 mg (50%) of the desired product were obtained. — $^1$H—NMR (270 MHz, DMSO): δ=1.13 (d, 3H, CH—CH$_3$); 1.65 and 1.92 (2×mc, 2×1H, CH$_2$—CH$_2$—CH); 2.84-3.05 (m, 3H, CH$_2$—CH$_2$—CH); 3.20 (dd, 1H, H-6); 3.95 (mc, 1H, CH—CH$_3$); 4.10 (dd, 1H, H-5); 4.95 (d, 1H, OH); 6.91-7.04 (m, 3H, aromatic H); 7.65 (d, 1H, aromatic H).

EXAMPLE 2

Potassium (1S,5R,6S)-6-[(1R)-1-hydroxyethyl]-(1,2,3,4tetrahydronaphtho)[2,1-a ]carbapen-2-em-3-carboxylate.

Step 1

(3S ,4R)-1-[(Allyloxycarbonyl)-hydroxymethyl ]-3-[( 1R)-1-tert-butyldimethylsilyloxyethyl]-4-[(2R)-1-oxo-1,2,3,4-tetrahydronaphth-2-yl ]azetidin-2-one.

1.23 g (10.8 mmol) of allyl glyoxalate were added under argon to a solution of 2.0 g (5.35 mmol) of the azetidinone (see step 1 of Example 1) in 6 ml of anhydrous THF and 0.21 ml (1.5 mmol) of triethylamine was then slowly added dropwise via a syringe. After 4 h at room temperature, the reaction mixture was poured into ice-water, the organic phase was separated off and the aqueous phase was extracted several times with ethyl acetate. The solvent was removed on a rotary evaporator and the crude product was directly reacted further in step 2.

Step 2

(3S,4R)-1-[(Allyloxycarbonyl)-chloromethyl ]-3-[(1R)-1-tert-butyldimethylsilyloxyethyl]-4-[(2R)-1-oxo-1,2,3,4-tetrahydronaphth-2-yl ]azetidin-2-one.

1.55 ml (1.43 g, 13.3 mmol) of 2,6-lutidine were added at $-30°$ C. to the solution of 2.0 g of the hydroxy compound in 40 ml of THF. 0.85 ml (1.39 g, 11.6 mmol) of thionyl chloride in 5 ml of THF was added dropwise and the mixture was stirred at the given temperature for 1 h. The reaction mixture was concentrated in an oil pump vacuum, the residue was taken up in ethyl acetate and the product was separated off from insoluble constituents by filtration. After removal of the solvent on a rotary evaporator, the crude substance was immediately employed further in step 3.

Step 3

(3S, 4R)-1-[(Allyloxyaarbonyl)-triphenylphosphoranylidenemethyl]-3-[(1R)-1-tert-butyldimethylsilyloxyethyl]-4-[(2R)-1-oxo-1,2,3,4-tetrahydronaphth-2-yl]azetidin-2-one.

1.3 g (4.96 mmol) of triphenylphosphine were added to a solution of the chloro compound in 6 ml of DMF and the mixture was stirred at room temperature for 60 min. 30 ml of ethyl acetate were then added to the reaction mixture and it was washed three times with 20 ml of a dil. $NaHCO_3$ solution each time. The organic phase was dried over $MgSO_4$ and the solvent was removed in vacuo. Chromatography on silica gel (eluent: toluene/ethyl acetate=5:1 to 2:1) gave 905 mg (23%, over three steps) of the phosphorane. —MS (FAB): m/e=738 (M+Li), 732 (M+H+).

Step 4

Allyl (1S,5R,6S)-6-[(1R)-1-tert-butyldimethylsilyloxyethyl]-(1,2,3,4-tetrahydronaphtho)[2,1-a]carbapen-2-em-3-carboxylate.

A solution of 893 mg (1.22 mmol) of phosphorane in 20 ml of mesitylene was heated at 160° C. for 3 h. The solvent was removed in vacuo and the crude product was chromatographed on silica gel (eluent: toluene/ethyl acetate=30:1). Yield: 141 mg (25%). According to $^1$H-NMR data, the compound is identical to the product from Example 1/step 3.

EXAMPLE 3

Potassium (1S,5R,6S)-6-[(1R)-1-hydroxyethyl]-(1,2,3,4-tetrahydronaphtho)[2,1-a ]carbapen-2-em-3-carboxylate.

Step 1

Allyl [(3S,4R)-3-[(1R)-1-hydroxyethyl]-4-[(2R)-1-oxo-1,2,3,4-tetrahydronaphth-2-yl)]-2-oxoazetidin-1-yl]-2-oxoacetate.

109 mg (0.78 mmol) of boron trifluoride etherate were added dropwise at $-40°$ C. in the course of 20 min to a solution of 250 mg (0.52 mmol) of the N-oxalyl compound (product from step 2 of Example 1) in 5 ml of acetonitrile. After a further 2 h at this temperature, 10 ml of dil. $NaHCO_3$ soln. were added to the reaction mixture and the mixture was extracted with ethyl acetate. The organic phases were dried over $MgSO_4$ and the solvent was removed in vacuo. The crude product was directly reacted further to give the silyl ether.

Step 2

Allyl [(3S,4R)-3-[(1R)-1-trimethylsilyloxyethyl]-4-[(2R)-1-oxo-1,2,3,4-tetrahydronaphth-2-yl)]-2-oxoazetidin-1-yl]-2-oxoacetate.

177 mg (0.44 mmol) of the hydroxy compound, dissolved in 1 ml of methylene chloride, were slowly added to a mixture of 67 mg (0.66 mmol) of triethylamine and 72 mg (0.66mmol) of chlorotrimethylsilane in 2 ml of methylene chloride and it was stirred at room temperature for 2.5 h. The solvent was removed in an oil pump vacuum and the residue was chromatographed on silica gel (eluent: toluene/ethyl acetate=30:1). Yield: 64 mg (28%, over both steps) of silyl etcher. — $^1$H-NMR (270 MHz, $CDCl_3$): $\delta=0.10$ (s, 9H, $SiCH_3$); 1.20 (d, 3H, $CH-CH_3$); 1.98–2.30 (m, 2H, $CH-CH_2-CH_2$); 3.06–3.24 (m, 3H, $CH-CH_2-CH_2$); 3.32 (dd, 1H, H-3); 4.29 (mc, 1H, $CH-CH_3$); 4.58 (dd, 1H, H-4); 4.82 (d, 2H, $CH_2-CH=CH_2$); 5.29–5.47 (m, 2H, $CH_2-CH=CH_2$); 5.98 (mc, 1H, $CH_2-CH=CH_2$); 7.22–7.35 (m, 2H, aromatic H); 7.50 (mc, 1H, aromatic H); 8.03 (d, 1H, aromatic H).

Step 3

Allyl (1S,5R,6S)-6-[(1R)-1-trimethylsilyloxyethyl]-(1,2,3,4-tetrahydronaphtho ) [2,1-a]carbapen-2-em-3-carboxylate.

131 mg (0.30 mmol) of trimethylsilyl ether were reacted with diethyl methanephosphonite as described in Example 1 under step 3. After chromatographic purification (silica gel, eluent: toluene/ethyl acetate=30:1), 33 mg (27%) of cyclization product were obtained. — $^1$H-NMR (270 MHz, $CDCl_3$): $\delta=0.16$ (s, 9H, $SiCH_3$); 1.28 (d, 3H, $CH-CH_3$); 1.53–2.15 (m,-2H, $CH-CH_2-CH_2$); 3.07 (mc, 2H, $CH-CH_2-CH_2$); 3.19 (mc, 1H, $CH-CH_2-CH_2$); 3.29 (dd, 1H, H-6); 4.18–4.32 (m, 2H, H-5 and $CH-CH_3$); 4.79 (mc, 2H, $CH_2-CH=CH_2$); 5.22–5.47 (m, 2H, $CH_2-CH=CH_2$); 5.99 (mc, 1H, $CH_2-CH=CH_2$); 7.10–7.28 (m, 3H, aromatic H); 7.76 (d, 1H, aromatic H).

Step 4

Allyl (1S,5R,6S)-6-[(1R)-1-hydroxyethyl]-(1,2,3,4-tetrahydronaphtho)[2,1-a ]carbapen-2-em-3-carboxylate.

The silyl protective group was cleaved with tetrabutylammonium fluoride trihydrate analogously to step 4 in Example 1. However, the reaction was already complete after 30 min at room temperature. Starting from 30 mg (0.07 mmol) of substrate, 12 mg (49%) of the hydroxy compound were obtained after chromatography on silica gel (eluent: toluene/ethyl acetate=3:1). According to the $^1$H-NMR comparison spectrum, the product is identical to the product from Example 1/step 4.

The cleavage of the allyl ester to give the potassium salt has already been described in Example 1 under step 5.

EXAMPLE 4

Potassium (1R,5R,6S)-6-[(1R)-1-hydroxyethyl]-(1,2,3,4-tetrahydronaphtho)[2,1-a]carbapen-2-em-3-carboxylate.

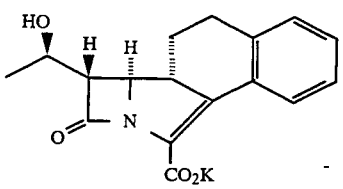

Step 1

(3S ,4R)-3-[(1R)-1-tert-Butyldimethylsilyloxyethyl]-4-[(2S)-1-oxo-1,2,3,4-tetrahydronaphth-2-yl]azetidin-2-one.

The crude product obtained in step 1 under Example 1 was chromatographed on silica gel (eluent: toluene-/ethyl acetate=4:1). After crystallization from n-heptane, the less polar α-diastereomer was obtained in 14% yield. M.p. (heptane) 152° C. —$^1$H-NMR (270 MHz, CDCl$_3$): δ=0.06 and 0.09 (2×s, 2×3H, SiCH$_3$); 0.89 (s, 9H, SiC(CH$_3$)$_3$); 1.28 (d, 3H, CH—C$_3$); 1.79–1.98 and 2.24–2.46 (2×m, 2×1H, CH—CH$_2$—CH$_2$); 2.55 (mc, 1H, CH—CH$_2$—CH$_2$); 2.86 (mc, 1H, H-3); 2.96–3.19 (m, 2H, CH—CH$_2$—CH$_2$); 3.73 (dd, 1H, H-4); 4.20 (mc, 1H, CH—CH$_3$); 6.45 (br, 1H, NH); 7.24–7.39 (m, 2H, aromatic H); 7.51 (t, 1H, aromatic H); 8.01 (d, 1H, aromatic H).

Step 2

Allyl [(3S,4R)-3-[(1R)-1-tert-butyldimethylsilyloxyethyl]-4-[(2S)-1-oxo-1,2,3,4-tetrahydronaphth-2-yl]-2-oxoazetidin-1-yl]-2-oxoacetate.

5 g (13.4 mmol) of azetidin-2-one were acylated as described in Example 1 under step 2. After chromatography on silica gel (eluent: heptane/ethyl acetate=4:1), 6.06 g (93%) of oily product were obtained. —$^1$H-NMR (270 MHz, CDCl$_3$): δ=0.05 and 0.10 (2×s, 2×3H, SiCH$_3$); 0.88 (s, 9H, SiC(CH$_3$)$_3$); 1.30 (d, 3H, CH—CH$_3$); 1.95–2.12 and 2.20–2.33 (2×m, 2×1H, CH—CH$_2$—CH$_2$); 3.04–3.11 (m, 2H, CH—CH$_2$'CH$_2$); 3.18 (m, 1H, H-3); 3.51 (mc, 1H, CH—CH$_2$—CH$_2$); 4.37 (mc, 1H, CH—CH$_3$); 4.81 (2H, d, CH$_2$—CH=CH$_2$); 5.13 (mc, 1H, H-4); 5.33 and 5.42 (2×d, 2×1H, CH$_2$—CH=CH$_2$); 5.98 (mc, 1H, CH$_2$—CH=CH$_2$); 7.22–7.38 (m, 2H, aromatic H); 7.51 (t, 1H, aromatic H); 8.03 (d, 1H, aromatic H).

Step 3

Allyl (1R,5R,6S)-6-[(1R)-1-tert-butyldimethylsilyloxyethyl]-(1,2,3,4-tetrahydronaphtho)[2,1-a]carbapen-2-em-3-carboxylate.

6.0 g (12.4 mmol) of allyl ester in 150 ml of anhydrous xylene were reacted at 140° C. with 10.2 g (37.2 mmol) of diethyl methanephosphonite. After concentration in a high vacuum and chromatography on silica gel (eluent: toluene/ethyl acetate=98:2), 346 mg (6%) of product were obtained. —$^1$H-NMR (270 MHz, CDCl$_3$): δ=0.09 and 0.10 (2×s, 2×3H, SiCH$_3$); 0.90 (s, 9H, SiC(CH$_3$)$_3$); 1.28 (d, 3H, CH—CH$_3$); 1.85–2.05 and 2.18–2.30 (2×m, 2×1H, CH—CH$_2$—CH$_2$); 2.95–3.03 (m, 2H, CH—CH$_2$—CH$_2$); 3.18 (dd, 1H, H-6); 3.29 (mc, 1H, CH—CH$_2$—CH$_2$); 3.78 (dd, 1H, H-5); 4.24 (mc, 1H, CH—CH$_3$); 4.77 (mc, 2H, CH—CH=CH$_2$); 5.25 and 5.44 (2×d, 2×1CH$_2$—CH$_2$=CH); 5.99 (mc, 1H, CH$_2$—CH—CH$_2$); 6.95–7.30 (m, 3H, aromatic H); 8.48 (d, 1H, aromatic H).

Step 4

Allyl (1R, 5R, 6S)-6-[(1R)-1-hydroxyethyl]-(1,2,3,4-tetrahydronaphtho)[2,1-a]carbapen-2-em-3-carboxylate.

The cleavage of the silyl ether was carried out as described under Example 1 as step 4. From 330 mg (0.73 mmol) of silyl ether, 145 mg (59%) of product were obtained and were employed directly in step 5.

Step 5

Potassium (1R,5R,6S)-6-[(1R)-1-hydroxyethyl]-(1,2,3,4tetrahydronaphtho)[2,1-a ]carbapen-2-em-3-carboxylate.

Starting from 145 mg (0.43 mmol) of allyl ester, 104 mg (72%) of potassium salt were obtained after freeze-drying analogously to step 5 in Example 1. —$^1$H-NMR (270 MHz, D$_2$O): δ=1.32 (d, 3H, CH—CH$_3$); 1.68–1.86 and 2.21–2.33 (2×m, 2×1H, CH—CH$_2$—CH$_2$); 2.89–2.98 (m, 2H, CH—CH$_2$—CH$_2$); 3.36 (mc, 1H, CH—CH$_2$—CH$_2$); 3.47 (dd, 1H, H-6); 3.88 (dd, 1H, H-5); 4.25 (mc, 1H, CH—CH$_2$); 7.16–7.30 (m, 3H, aromatic H); 7.95 (d, 1H, aromatic H).

EXAMPLE 5

Potassium (1S,5R,6S)-6-[(1R)-1-hydroxyethyl]-(7-fluoro-1,2,3,4-tetrahydronaphtho)[2,1-a]carbapen-2-em-3-carboxylate.

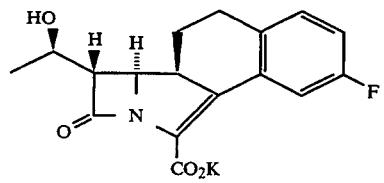

Step 1

(3S ,4R)-3-[(1R)-1-tert-Butyldimethylsilyloxyethyl]-4-[(2R ) -7-fluoro-1-oxo-1,2,3,4-tetrahydronaphth-2-yl]-azetidin-2-one.

9.9 g (40mmol) of 2-bromo-7-fluorotetralone were reacted as was described for step 1 in Example 1. After chromatography on silica gel (eluent: toluene/ethyl acetate=4:1), 810 mg (8%) of product were obtained. —$^1$H-NMR (270 MHz, CDCl$_3$): δ=0.09 (s, 6H, SiCH$_3$); 0.88 (s, 9H, SiC(CH$_3$)$_3$); 1.27 (d, 3H, CH—CH$_3$); 1.96–2.15 and 2.22–2.35 (2×m, 2×1H, CH—CH$_2$—CH$_2$); 2.73 (mc, 1H, CH—CH$_2$—CH$_2$); 3.02–3.13 (m, 3H, H-3, CH—CH$_2$—CH$_2$); 4.27 (mc, 1H, CH—CH$_3$); 4.43 (dd, 1H, H-4); 5.82 (br, 1H, NH); 7.16–7.30 (m, 2H, aromatic H); 7.67 (dd, 1H, aromatic

Step 2

Allyl [(3S,4R)-3-[(1R)-1-tert-butyldimethylsilyloxye]-4- [(2R)-7- fluoro-1-oxo-1,2,3,4-tetrahydronaphth-2-yl]-2-oxoazetidin-1-yl]-2-oxoacetate.

Analogously to step 2 in Example 1, 890 mg(92%) of allyl ester were synthesized from 756 mg (1.93 mmol) of azetidin-2-one. M.p. 100°–101° C. —$^1$H-NMR (270 MHz, CDCl$_3$): δ=0.07 and 0.09 (2×s, 2×3H, SiCH$_3$); 0.86 (s, 9H, SiC(CH$_3$)$_3$); 1.20 (d, 3H, CH—CH$_3$); 1.92–2.10 and 2.20–2.32 (2×m, 2×1H, CH—CH$_2$—CH$_2$); 3.01–3.12 (m, 2H, CH—CH$_2$—CH$_2$); 3.17 (mc, 1H, CH—CH$_2$—CH$_2$); 3.29 (mc, 1H, H-3); 4.33 (mc, 1H, CH—CH$_3$); 4.69 (mc, 1H, H-4 ); 4.80 (d, 2H, $CH_2$—CH=$CH_2$); 5.31 and 5.41 (2×d, 2×1H, $CH_2$—CH=$CH_2$); 5.97 (mc, 1H, $CH_2$—CH—$CH_2$); 7.15–7.28 (m, 2H, aromatic H); 7.70 (dd, 1H, aromatic H).

Step 3

Allyl (1S,5R,6S)-6-[(1R)-1-tert-butyldimethylsilyloxyethyl]-(7-fluoro-1,2,3,4-tetrahydronaphtho)[2,1-a]-carbapen-2-em-3-carboxylate.

Cyclization of 870 mg (1.73 mmol) of allyl ester was carried out as described in Example 1. The mixture was worked up after 45 minutes at 160° C. After chromatography, 326 mg (40%) of product were obtained. — $^1$H-NMR (270 MHz, $CDCl_3$): δ=0.10 (s, 6H, $SiCH_3$); 0.90 (s, 9H, $SiC(CH_3)_3$); 1.27 (d, 3H, CH—$CH_3$); 1.82–2.14 (m, 2H, CH—$CH_2$—$CH_2$); 2.97–3.06 (m, 2H, CH—$CH_2$—$CH_2$); 3.17 (mc, 1H, CH—$CH_2$—$CH_2$); 3.28 (dd, 1H, H-6); 4.27 (mc, 1H, CH—$CH_3$); 4.32 (dd, 1H, H-5); 4.78 (mc, 2H, $CH_2$—CH=$CH_2$); 5.27 and 5.42 (2×d, 2×1H, $CH_2$—CH=$CH_2$); 5.98 (mc, 1H, $CH_2$—CH—$CH_2$); 6.94 (dt, 1H, aromatic H); 7.08 (dd, 1H, aromatic H); 7.54 (dd, 1H, aromatic H).

Step 4

Allyl (1S,5R,6S)-6-[(1R)-1-hydroxyethyl]-(7-fluoro-1,2,3,4-tetrahydronaphtho)[2,1-a]carbapen-2-em-3-carboxylate.

The hydroxyethyl compound (1.18 mg, 50%) was prepared from 10 mg (0.66 mmol) of silyl ether analogously to step 4 in Example 1. This compound was immediately further reacted.

Step 5

Potassium (1S,5R,6S)-6-[(1R)-1-hydroxyethyl]-(7-fluoro-1,2,3,4-tetrahydronaphtho)[2,1-a]carbapen-2-em-3-carboxylate.

47 mg (40%) of potassium salt were obtained from 117 mg (0.33 mmol) of allyl ester analogously to step 5 in Example 1. — $^1$H-NMR (270 MHz, $D_2O$): δ=1.30 (d, 3H, CH—$CH_3$); 1.72–1.93 and 2.05–2.20 (2×m, 2×1H, CH—$CH_2$—$CH_2$); 2.90–3.05 (m, 2H, CH—$CH_2$—$CH_2$); 3.25 (mc, 1H, CH—$CH_2$—$CH_2$); 3.58 (dd, 1H, H-6); 4.28 (mc, 1H, CH—$CH_3$); 4.38 (dd, 1H, H-5); 6.98 (dt, 1H, aromatic H); 7.15–7.28 (m, 2H, aromatic H).

EXAMPLE 6

Sodium (1S, 5R, 6S)-6-[(1R)-1-hydroxyethyl]-(4,4-dimethyl-1,2,3,4-tetrahydronaphtho)[2,1-a]carbapen-2-em-3-carboxylate.

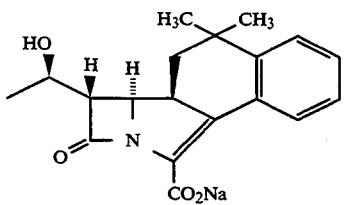

Step 1

(3S,4R)-3-[(1R)-1-tert-Butyldimethylsilyloxyethyl]-4-[(2RS)-4,4-dimethyl-1-oxo-1,2,3,4-tetrahydronaphth-2-yl]-azetidin-2-one.

7.5 g (30 mmol) of 2-bromo-4,4-dimethyltetralone were reacted in analogy to Example 1/step 1. According to —$^1$H-NMR, the crude product contained the two isomers in the ratio α/β=1:3. The isomer mixture was obtained after chromatography on silica gel (deactivated with 10% $H_2O$, eluent: toluene/ethyl acetate=5:1). Yield: 5.4 g (59%). —$^1$H-NMR (270 MHz, $CDCl_3$): δ=0.10 (s, 6H, $SiCH_3$); 0.89 (s, 9H, $SiC(CH_3)_3$); 1.32 (d, 3H, CH—$CH_3$); 1.39 (s, H, $CH_3$, β-compound); 1.41 (s, 3H, $CH_3$, α-compound); 1.45 (s, 3B, $CH_3$, α-compound); 1.47 (s, 3H, $CH_3$, β-compound); 1.85–2.20 (m, 2H, six-membered ring H); 2.90–3.03 (m, 1H, six-membered ring H); 3.05 (dd, 1H, B-3); 3.68 (dd, 1H, H-4, α-compound); 4.20–4.35 (m, 1H, CH—$CH_3$); 4.46 (dd, 1H, H-4, β-compound); 5.73 (s, 1H, NH, β-compound); 6.50 (s, 1H, NH, α-compound); 7.25–7.62 and 7.90–8.05 (m, 4H, aromatic H).

Step 2

Allyl[(3S,4R)-3-[(1R)-1-tert-butyldimethylsilyloxyethyl]-4-[(2R, S)-4,4-dimethyl-1-oxo-1,2,3,4-tetrahydronaphth-2-yl]-2-oxoazetidin-1-yl]-2-oxoacetate.

3.0 g (7.5 mmol) of azetidinone were reacted in analogy to Example 1/step 2. According to $^1$H-NMR the product contained the two isomers in the ratio α/β=1:4. Yield: 3.1 g (80%). $^1$H-NMR (270 MHz, $CDCl_3$): δ=0.08 and 0.11 (2×s, 2×3H, $SiCB_3$); 0.88 (s, 9H, $SiC(CH_3)_3$); 1.25 (d, 3H, CH—$CH_3$); 1.41 (s, 3H, $CH_3$); 1.48 (s, 3H, $CH_3$); 1.80–2.00 (m, 2H, six-membered ring H); 3.20 (mc, 1H, H-3, α-compound); 3.26 (mc, 1H, H-3, β-compound); 3.45–3.65 (m, 1H, six-membered ring H, β-compound); 3.54–2.75 (m, 1H, six-membered ring H, α-compound); 4.20–4.40 (m, 1H, CH—$CH_3$); 4.57 (mc, H-4, β-compound); 4.70–4.90 (m, 2H, -$CH_2$—CH=$CH_2$); 5.10 (mc, 1H, H-4, α-compound); 5.10–5.50 (m, 2H, —$CH_2$—CH=$CH_2$); 5.85–6.10 (m, 1H, —$CH_2$—CH=$CH_2$); 7.10–7.60 and 7.90–8.05 (m, 4H, aromatic H).

Step 3

Allyl (1S,5R,6S)-6-[(1R)-1-tert-butyldimethylsilyloxymethyl]-(4,4-dimethyl-1,2,3,4-tetrahydronaphtho)[2,1-a]-carbapen-2-em-3-carboxylate.

3.8 g (7.5 mmol) of allyl ester were cyclized in analogy to Example 1/step 3. According to $^1$H-NMR the product exclusively contained the β-isomer. Yield: 2.4 g (68%). — $^1$H-NMR (270 MHz, $CDCl_3$): δ=0.10 (s, 6H, $SiCH_3$); 0.90 (s, 9H, $SiC(CH_3)_3$); 1.28 (d, 3H, CH—$CH_3$); 1.40 (s, 3H, $CH_3$); 1.49 (s, 3H, $CH_3$); 1.75–1.93 (m, 2H, six-membered ring H); 3.15–3.40 (m, 2H, six-membered ring H and H-6); 4.15–4.40 (m, 2H, CH—$CH_2$and H-5); 4.60–4.90 (m, 2H, $CH_2$—CH=$CH_2$); 5.20–5.50 (m, 2H, $CH_2$—CH=$CH_2$); 5.85–6.10 (m, 1H, $CH_2$—CH=$CH_2$); 7.10–7.40 and 7.70–7.80 (m, 4H, aromatic H).

Step 4

Allyl (1S,5R,6S)-6-[(1R)-1-hydroxyethyl]-(4,4-dimethyl-1,2,3,4-tetrahydronaphtho)[2,1-a]carbapen-2-em-3-carboxylate.

400 mg (0.83 mmol) of silyl ether were reacted in analogy to Example 1/step 4. Yield: 60 mg (20%). —$^1$H-NMR (270 MHz, $CDCl_3$): δ=1.34 (s, 3H, $CH_3$); 1.36 (d, 3H, CH—$CH_3$); 1.43 (s, 3H, CH3); 1.70–1.90 (m, 2H, six-membered ring H); 2.75–3.05 (m, 1H, six-membered ring H); 3.18 (dd, 1H, H-6); 3.92 (dd, 1H, H-5); 4.15–4.30 (m, 1H, CH—$CH_3$); 4.60–4.75 (m, 2H, $CH_2$—CH=$CH_2$); 5.10–5.25 (m, 2H, $CH_2$—CH=$CH_2$); 5.70–5.90 (m, 1H, $CH_2$—$CH_2$=$CH_2$); 7.10–7.40 (m, 4H, aromatic H).

Step 5

Sodium (1S, 5R, 6S)-6-[(1R)-1-hydroxyethyl]-(4,4-dimethyl-1,2,3,4-tetrahydronaphtho)[2,1-a]carbapen-2-em-3-carboxylate.

50 mg (0.14 mmol) of allyl ester were reacted in analogy to Example 1/step 5. Yield: 45 mg (92%). —¹H-NMR (270 MHz, D₂O): δ=1.28 (d, 3H, CH—CH₃); 1.32 and 1.42 (2×s, 2×3H, CH₃); 1.82 (s, 1H, six-membered ring H); 1.86 (d, 1H, six-membered ring H); 3.08 (mc, 1H, six-membered ring H); 3.42 (dd, 1H, H-6); 3.96 (dd, 1H, H-5); 4.23 (mc, 1H, CH—CH₃); 7.14–7.30 (m, 2H, aromatic H); 7.39 (dt, 1H, aromatic H); 7.52 (d, 1H, aromatic H).

EXAMPLE 7

Potassium (1R,5R,6S)-6-[(1R)-1-hydroxyethyl]-(chromano)[3,4-a]carbapen-2-em-3-carboxylate.

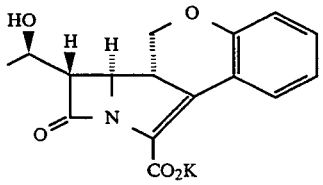

Step 1

(3S,4R)-3-[(1R)-1-tert-Butyldimethylsilyloxyethyl]-4-[(3R)-4-oxochroman-3-yl]azetidin-2-one.

3.40 g (15 mmol) of 3-bromochroman-4-one were reacted analogously to step 1 in Example 1. According to HPLC, the crude product contained the two isomers in the ratio α/β=1:3. It was possible to separate the two isomers by column chromatography (silica gel, eluent: toluene/ethyl acetate=3:1). 0.50 g (13%) of the α-isomer was isolated. —¹H-NMR (270 MHz, CDCl₃): δ=0.09 (s, 6H, SiCH₃); 0.89 (s, 9H, SiC(CH₃)₃); 1.28 (d, 3H, CH—CH₃); 2.86 (mc, 1H, O—CH₂—CH); 2.94 (mc, 1H, H-3); 3.71 (dd, 1H, H-4); 4.18 (mc, 1H, CH—CH₃); 4.29 and 4.61 (2×1H, —O—CH₂—CH); 6.78 (bs, 1H, NH); 7.02 (mc, 2H, aromatic H); 7.50 (mc, 1H, aromatic H); 7.88 (mc, 1H, aromatic H).

Step 2

Allyl [(3S,4R)-3-[(1R)-1-tert-butyldimethylsilyloxyethyl]-4-[(3R)-4-oxochroman-3-yl]-2-oxoazetidin-1-yl]-2oxoacetate.

1.00 g (2.66 mmol) of the azetidinone was reacted with allyl oxalyl chloride analogously to step 2 in Example 1. After column chromatography on silica gel (deactivated with 10% H₂O, eluent: toluene/ethyl acetate=30:1), 1.25 g (96%) of oil were obtained. —¹H-NMR (270 MHz, CDCl₃): δ=0.05 (s, 6H, SiCH₃); 0.84 (s, 9H, SiC(CH₃)₃); 1.02 (d, 3H, CH—CH₃); 3.50 (m, 1H, O—CH₂—CH and H-3); 4.24 (mc, 1H, CH—CH₃); 4.60–4.80 (m, 3H, O—CH₂—CH and H-4); 4.82 (mc, 2H, CH₂—CH═CH₂); 5.37 (mc, 2H, CH₂—CH═CH₂); 5.96 (mc, 1H, CH₂—CH═CH₂); 7.02 (mc, 2H, aromatic H); 7.50 (mc, 1H, aromatic H); 7.79 (d, 1H, aromatic H).

Step 3

Allyl (1S,5R,6S)-6-[(1R)-1-tert-butyldimethylsilyloxyethyl]-(chromano)[3,4a]carbapen-2-em-3-carboxylate.

1.30 g (2.66 mmol) of allyl ester were reacted in anhydrous xylene, as described in Example 1 under step 3. After chromatography on silica gel (eluent: toluene-/ethyl acetate=50:1), 250 mg (20%) were isolated as an oil. —¹H-NMR (270 MHz, CDCl₃): δ=0.10 (s, 6H, SiCH₃); 0.89 (s, 9H, SiC(CH₃)₃); 1.28 (dr 3H, CH—CH₃); 3.24 (dd, 1H, H-6); 3.60–3.71 (m, 1H, OCH₂—CH); 3.77 (dd, 1H, H-5); 4.11 (dd, 1H, O—CH₂—CH); 4.22 (mc, 1H, CH—CH₃); 4.59 (dd, 1H, O—CH₂—CH); 4.70–4.90 (m, 2H, CH₂—CH═CH₂); 5.25–5.52 (m, 2H, CH₂—CH═CH₂); 5.90–6.10 (m, 1H, CH₂—CH═CH₂); 6.8–57.00 (m, 2H, aromatic H); 7.31 (mc, 1H, aromatic H); 8.60 (d, 1H, aromatic H).

Step 4

Allyl (1S,5R,6S)-3-[(1R)-1-hydroxyethyl]-(chromano)[3,4a]carbapen-2-em-3-carboxylate.

250 mg (0.55 mmol) of the silyl ether were reacted analogously to step 4 in Example 1. After chromatography (silica gel, eluent: toluene/ethyl acetate=1:2), 300 mg of yellow oil were obtained and immediately further reacted.

Step 5

Potassium (1R,5R,6S)-6-[(1R)-1-hydroxyethyl]-(chromano)[3,4-a]carbapen-2-em-3-carboxylate.

300 mg of the crude allyl ester were reacted analogously to step 5 in Example 1. After chromatography (®LiChroprep RP 18, eluent: water), 100 mg (54% based on step 3) were isolated as a yellow solid. —¹H-NMR (270 MHz, D₂O): δ=1.31 (d, 3H, CH—CH₃); 3.57 (dd, 1H, OCH₂—CH); 3.67 (mc, 1H, H-1); 3.89 (dd, 1H, H-5); 4.05 (dd, 1H, O—CH₂—CH); 4.24 (mc, 1H, CH—CH₃); 4.65 (dd, 1H, O—CH₂—CH); 6.90–700 (m, 2H, aromatic H); 720–7.30 (m, 1H, aromatic H); 8.13 (m, 1H, aromatic H)

EXAMPLE 8

Potassium (1S,5R,6S)-6-[(1R)-1-hydroxyethyl]-(thio-chromano)[3,4-a]carbapen-2-em-3-carboxylate.

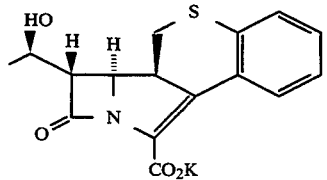

Step 1

(3S, 4R)-3-[(1R)-1-tert-Butyldimethylsilyloxyethyl]-4-[(3R)-4-oxothiochroman-3-yl]azetidin-2-one.

4.86 g (20mmol) of 3-bromothiochroman-4-one were reacted analogously to step 1 in Example 1. It was possible to separate the two isomers by column chromatography (silica gel, eluent: toluene/ethyl acetate=6:1). 1.36 g (17%) of the β-isomer were isolated. —¹H-NMR (270 MHz, CDCl₃): δ=0.09 (s, 6H, SiCH₃); 0.88 (s, 9H, SiC(CH₃)₃); 1.14 (d, 3H, CH—CH₃); 3.01 (mc, 1H, S—CH₂—CH); 3.12 (dd, 1H, H-3); 3.25–3.31 (m, 2H, S—CH₂—CH); 4.25 (mc, 1H, CH—CH₃); 4.48 (dd, 1H, H-4); 5.89 (bs, 1H, NH); 7.13–7.45 (m, 3H, aromatic H); 8.06 (d, 1H, aromatic H).

Step 2

Allyl [(3S, 4R)-3-[(1R)-1-tert-butyldimethylsilyloxyethyl]-4-[(3R)-4-oxothiochroman-3-yl]-2-oxoazetidin-lyl]-2-oxoacetate.

1.35 g (3.45 mmol) of the azetidinone were reacted with allyl oxalyl chloride analogously to step 2 in Example 1. After column chromatography on silica gel (deactivated with 10% H₂O, eluent: toluene/ethyl acetate=3:1), 1.43 g (82%) of yellow solid were obtained. —¹H-NMR (270 MHz, CDCl₃): δ=0.07 (s, 6H, SiCH₃); 0.82 (s, 9H, SiC(CH₃)₃); 1.04 (d, 3H, CH—CH₃); 3.31–3.38 (m, 3H, S—CH₂—CH and S—CH₂—CH); 3.41 (dd, 1H, H-3); 4.31 (mc, 1H, CH—CH₃); 4.81 (mc, 2H, CH₂—CH═CH₂); 4.92 (mc, 1H, H-4); 5.30–5.47 (m, 2H, CH₂—CH═CH₂); 5.96

(mc, 1H, CH₂—CH=CH₂); 7.12–7.42 (m, 3H, aromatic H); 8.08 (d, 1H, aromatic H).

Step 3

Allyl (1S,5R,6S)-3-[(1R)-1-tert-butyldimethylsilyloxyethyl]-(thiochromano)[3,4-a]carbapen-2-em-3-carboxylate.

2.02 g (4.0 mmol) of allyl ester were reacted as described in Example 1 under step 3. After chromatography on silica gel (eluent: toluene/ethyl acetate=50:1), 930 mg (49%) were isolated as a yellow solid. —¹H-NMR (270 MHz, CDCl₃): δ=0.10 (s, 6H, SiCH₃); 0.90 (s, 9H, SiC(CH₃)₃); 1.28 (d, 3H, CH—CH₃); 2.98 (dd, 1H, H-6); 3.19–3.38 (m, 3H, S—CH₂—CH and S—CH₂—CH); 4.28 (mc, 1H, CH—CH₃); 4.39 (dd, 1H, H-5); 4.76 (mc, 2H, CH₂—CH=CH₂); 5.31 (mc, 2H, CH₂—CH=CH₂); 5.91 (mc, 1H, CH₂—CH=CH₂); 6.97–7.22 (m, 3H, aromatic H); 7.53 (mc, 1H, aromatic H).

Step 4

Allyl (1S,5R,6S)-6-[(1R)-1-hydroxyethyl]-(thiochromano)[3,4-a]carbapen-2-em-3-carboxylate.

326 mg (0.69 mmol) of the silyl ether were reacted analogously to step 4 in Example 1. After chromatography (silica gel, eluent: toluene/ethyl acetate=1:1), 161 mg (65%) of white solid were obtained. —¹H-NMR (270 MHz, CDCl₃): δ=1.39 (d, 3H, CH—CH₃); 3.02 (dd, 1H, H-6); 3.18–3.47 (m, 3H, S—CH₂—CH and S—CH₂—CH); 4.29 (mc, 1H, CH—CH₃); 4.41 (dd, 1H, H-5); 4.68–4.79 (m, 2H, CH₂—CH=CH₂); 5.23–5.42 (m, 2H, CH₂—CH=CH₂); 5.93 (m, 1H, CH₂—CH=CH₂); 6.98–7.21 (m, 3H, aromatic H); 7.53 (mc, 1H, aromatic H).

Step 5

Potassium (1S,5R,6S)-6-[(1R)-1-hydroxyethyl]-(thiochromano)[3,4-a]carbapen-2-em-3-carboxylate.

161 mg (0.45 mmol) of the allyl ester were reacted analogously to step 5 in Example 1. After chromatography (®LiChroprep RP 18, eluent: water), 64 mg (40%) of white solid were isolated. —¹H-NMR (270 MHz, D₂O): δ=1.31 (d, 3H, CH—CH₃); 3.10–3.42 (m, 3H, S—CH₂—CH and S—CH₂—CH); 3.56 (dd, 1H, H-6); 4.28 (mc, 1H, CH—CH₃); 4.43 (dd, 1H, H-5); 7.04–7.10 (m, 1H, aromatic H); 7.17–7.24 (m, 2H, aromatic H); 7.39 (mc, 1H, aromatic H).

EXAMPLE 9

Potassium (1S,5R,6S)-6-[(1R)-1-acetoxyethyl]-(1,2,3,4tetrahydronaphtho)[2,1-a]carbapen-2-em-3-carboxylate.

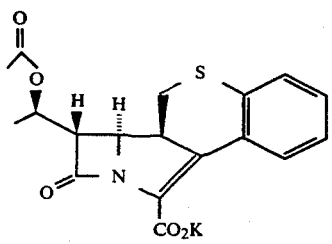

Step 1

(3S, 4R)-3-[(1R)-1-Acetoxyethyl]-4-[(2R)-1-oxo-1,2,3,4-tetrahydronaphtho)[2-yl]azetidin-2-one.

A total of 100 mg (0.62 mmol) of FeCl₃ was added in portions at 0° C. to a solution of 2.0 g (5.35 mmol) of silyl ether from Example 1/step 1 in 10 ml (10.82 g, 106 mmol) of acetic anhydride and the mixture was stirred with ice-cooling for 2.5 h. 25 ml of methylene chloride and 25 ml of water were added to this mixture, the organic phase was separated off and the aqueous phase was extracted twice with 10 ml of methylene chloride each time. After washing the organic phase with satd. NaHCO₃ solution and drying over MgSO₄, the crude product was chromatographed on silica gel (eluent: toluene/ethyl acetate=2:1). Yield: 1.56 g (97%). ¹H-NMR (270 MHz, CDCl₃): δ=1.42 (d, 3H, CH—CH₃), 1.94–2.11 (m, 1H, CH₂—CH₂—CH); 2.03 (s, 3H, COCH₃); 2.22–2.34 (m, 1H, CH₂—CH₂—CH); 2.73 (mc, 1H, CH₂—CH₂—CH); 3.11 (dd, 2H, CH₂—CH₂—CH); 3.20 (dd, 1H, H-3); 4.19 (dd, 1H, H-4); 5.33 (mc, 1H, CH—CH₃); 6.08 (bs, 1H, NH); 7.23–7.37 (m, 2H, aromatic H); 7.52 (mc, 1H, aromatic H); 8.01 (d, 1H, aromatic H).

Step 2

Allyl [(3S,4R)-3-[(1R)-1-acetoxyethyl]-4-[(2R)-1-oxo-1,2,3,4-tetrahydronaphth-2-yl]-2-oxoazetidin-1-yl]-2-oxoacetate.

1.45 g (4.8 mmol) of the azetidinone were reacted with allyl oxalyl chloride analogously to step 2 in Example 1. After column chromatography on silica gel (eluent: toluene/ethyl acetate=30:1), 1.62 g (81%) of product were isolated. —¹H-NMR (270 MHz, CDCl₃): δ=1.37 (d, 3H, CH—CH₃); 2.02–2.15 (m, 1H, CH₂—CH₂—CH); 2.20–2.30 (m, 1H, CH₂—CH₂—CH); 3.09–3.47 (m, 3H, CH₂—CH₂—CH); 3.51 (dd, 1H, H-3); 4.49 (dd, 1H, H-4); 4.85 (mc, 2H, CH₂—CH=CH₂); 5.30–5.48 (m, 2H, CH₂—CH=CH₂); 5.89–6.06 (m, 1H, CH₂—CH=CH₂ and CH—CH₃); 7.32–7.37 (m, 2H, aromatic H); 7.47–7.54 (m, 1H, aromatic H); 8.05 (d, 1H, aromatic H).

Step 3

Allyl (1S, 5R, 6S)-6- [(1R)-1-acetoxyethyl]-(1,2,3,4-tetrahydronaphtho)[2,1-a]carbapen-2-em-3-carboxylate.

245 mg (0.59 mmol) of allyl ester were reacted as described in Example 1 under step 3. After chromatography on silica gel (eluent: toluene/ethyl acetate=30:1), 55 mg (24%) of product were isolated as an oil. —¹H-NMR (270 MHz, CDCl₃): δ=1.41 (d, 3H, CH—CH₃); 1.85–2.16 (m, 2H, CH₂—CH₂—CH); 2.07 (s, 3H, COCH₃); 3.04–3.11 (m, 2H, CH₂—CH₂—CH); 3.20 (mc, 1H, CH₂—CH₂—CH); 3.47 (dd, 1H, H-6); 4.30 (dd, 1H, H-5); 4.79 (mc, 2H, CH₂—CH=CH₂); 5.21–5.46 (m, 3H, CH₂—CH=CH₂ and CH—CH₃); 5.91–6..08 (m, 1H, CH₂—CH=CH₂); 7.11–7.29 (m, 3H, aromatic H); 7.78 (d, 1H, aromatic H).

Step 4

Potassium (1S,5R,6S)-6-[(1R)-1-acetoxyethyl]-(1,2,3,4tetrahydronaphtho)[2,1-a]carbapen-2-em-3-carboxylate.

118 mg (0.31 mmol) of the allyl ester were reacted as described in Example 1 under step 5. The potassium salt was purified on ®LiChroprep RP18 (eluent: H₂O, then a gradient up to 15% CH₃CN). Yield: 49 mg (41%). —¹H-NMR (270 MHz, D₂O): δ=1.37 (d, 3H, CH—CH₃); 1.74–1.97 (m, 1H, CH—CH₂—CH₂); 2.05–2.23 (m, 1H, CH—CH₂—CH₂); 2.14 (s, 3H, COCH₃); 2.98–3.06 (m, 2H, CH—CH₂—CH₂); 3.23

(mc, 1H, CH—CH₂—CH₂); 3.55 (dd, 1H, H-6); 4.41 (dd, 1H, H-5); 5.30 (mc, 1H, CH—CH₃); 7.13–7.28 (m, 3H, aromatic H); 7.47 (d, 1H, aromatic H).

EXAMPLE 10

Sodium (1R,5R,6S)-6-[(1R)-1-hydroxyethyl]-(7-bromo-1,2,3,4-tetrahydronaphtho)[2,1-a]carbapen-2-em-3-carboxylate.

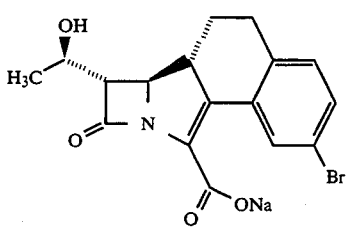

Precursor
2,7-Dibromo-1-tetralone.

34.8 g (155 mmol) of 7-bromo-1-tetralone were dissolved in 775 ml of dry diethyl ether. 8.0 ml (24.8 g, 155 mmol) of bromine were added dropwise in the course of 20 minutes. Immediate decolorization took place even on addition of the first drop. The mixture was subsequently stirred at room temperature for 1 h and then extracted by shaking with 9% strength sodium bicarbonate solution and saturated sodium chloride solution. After drying over magnesium sulfate, the solvent was stripped off on a rotary evaporator and the oily residue was dried to constant weight on the oil pump. Over the weekend crystals were obtained in the refrigerator, and were triturated in ethanol and filtered off with suction. After drying in a vacuum desiccator over phosphorus pentoxide, 30.6 g (65%) of brown crystals were obtained. M.p. 76°–77° C. —¹H-NMR (60 MHz, CDCl₃): δ=2.30–2.60 and 2.80–3.30 (2×m, 2×2H, CH₂—CH₂); 4.80 (mc, 1H, CHBr); 7.20 (d, 1H, aromatic H); 7.70 (dd, 1H, aromatic H); 8.31 (d, 1H, aromatic H).

Step 1

(3S,4R)-3-[(1R)-1-tert-Butyldimethylsilyloxyethyl]-4-[(2S)-7-bromo-1-oxo-1,2,3,4-tetrahydronaphth-2-yl]-azetidin-2-one.

5.0 g (16.4 mmol) of 2,7-dibromo-1-tetralone were reacted as was described for step 1 in Example 1. After chromatography on silica gel (eluent: toluene/ethyl acetate=5:1), 1.37 g (25%) of product were obtained. —¹H-NMR (270 MHz, CDCl₃): δ=0.07 and 0.09 (2×s, 6H, SiCH₃); 0.89 (s, 9H, SiC(CH₃)a); 1.28 (d, 3H, CH—CH₃); 1.70–2.20 (m, 1H, CH₂—CH₂—CB); 2.30 (mc, 1H, CH₂—CH₂—CH); 2.53 (mc, 1H, CH₂—CH₂—CH); 2.84 (mc, 1H, CH₂—CH₂—CH); 2.95–3.10 (m, 2H, CH₂—CH₂—CH and H-3); 3.71 (dd, 1H, H-4); 4.20 (mc, 1H, CH—CH₃); 6.42 (s, 1H, NH); 7.16 (d, 1H, aromatic B); 7.60 (dd, 1H, aromatic B); 8.12 (d, 1H, aromatic B).

Step 2

Allyl [(3S,4R)-3-[(1R)-1-tert-butyldimethylsilyloxyethyl]-4-[(2S)-7-bromo-1-oxo-1,2,3,4-tetrahydronaphth-2-yl]-2-oxoazetidin-1-yl]-2-oxoacetate.

Analogously to step 2 in Example 1, 800 mg (81%) of allyl ester were synthesized from 790 mg (1.75 mmol) of azetidin-2-one. —¹H-NMR (270 MHz, CDCl₃): δ=0.04 and 0.10 (2×s, 6H, SiCH₃); 0.88 (s, 9H, SiC(CH₃)₃); 1.29 (d, 3H, CH—CH₃); 1.90–2.10 (m, 1H, CH—CH₂—CH); 2.20–2.35 (m, 1H, CH₂—CH₂—CH); 2.95–3.10 (m, 2H, CH₂—CH₂—CH); 3.17 (mc, 1H, H-3); 3.49 (mc, 1H, CH₂—CH₂—CH); 4.35 (mc, 1H, CH—CH₃) 4.82 (mc, 2H, CH₂—CH=CH₂); 5.30–5.50 (m, 2H, CH₂—CH—CH₂); 5.85–6.10 (m, 1H, CH₂—CH—CH₂); 7.18 (d, 1H, aromatic 7.60 (dd, 1H, aromatic H); 8.15 (d, 1H, aromatic

Step 3

Allyl (1R,5R,6S)-6-[(1R)-1-tert-butyldimethylsilyloxyethyl]-(7-bromo-1,2,3,4-tetrahydronaphtho)[2,1-a]-carbapen-2-em-3-carboxylate.

Cyclization of 800 mg (1.42 mmol) of allyl ester was carried out as described in Example 1. After 45 minutes at 160° C., the mixture was worked up. After chromatography, 290 mg (38%) of product were obtained. —¹H-NMR (270 MHz, CDCl₃): δ=0.10 and 0.11 (2×s, 6H, SiCH₃); 0.90 (s, 9H, SiC(CH₃)₃); 1.28 (d, 3H, CH—CH₃); 1.80–2.00 (m, 1H, CH₂—CH₂—CH); 2.15–2.30 (m, 1H, CH₂—CH₂—CH); 2.87–3.00 (m, 2H, CH₂—CH); 3.19 (dd, 1H, H-6); 3.26 (mc, 1H, CH₂—CH₂—CH); 3.79 (dd, 1H, H-5); 4.22 (mc, 1H, CH—CH₃); 4.70–4.90 (m, 2H, CH₂—CH=CH₂); 5.22–5.55 (m, 2H, CH₂—CH=CH₂); 5.90–6.10 (m, 1H, CH₂—CH=CH₂); 7.02 (d, 1H, aromatic H); 7.38 (dd, 1H, aromatic H); 8.70 (d, 1H, aromatic H).

Step 4

Allyl (1R,5R,6S)-6-[(1R)-1-hydroxyethyl]-(7-bromo-1,2,3,4-tetrahydronaphtho)[2,1-a]carbapen-2-em-3-carboxylate.

The hydroxyethyl compound was prepared from 280 mg (0.53 mmol) of silyl ether analogously to step 4 in Example 1. After column chromatography on silica gel, 160 mg (73%) were obtained. —¹H-NMR (270 MHz, CDCl₃): δ=1.39 (d, 3H, CH—CH₃); 1.84–2.00 (m, 1H, CH₂—CH₂—CH); 2.20–2.40 (m, 1H, CH₂—CH₂—CH); 2.88–3.00 (m, 2H, CH₂—CH₂—CH); 3.20–3.35 (m, 2H, CH₂—CH₂—CH and H-6); 3.83 (dd, 1H, H-5); 4.26 (mc, 1H, CH—CH₃); 4.70–4.95 (m, 2H, CH₂—CH=CH₂); 5.23–5.55 (m, 2H, CH₂—CH—CH₂); 5.90–6.10 (m, 1H, CH₂—CH—CH₂); 7.04 (d, 1H, aromatic H); 7.40 (dd, 1H, aromatic H); 8.66 (d, 1H, aromatic H).

Step 5

Sodium (1R, 5R, 6S)-6-[(1R)-1-hydroxyethyl]-(7-bromo-1,2,3,4-tetrahydronaphtho)[2,1-a]carbapen-2-em-3-carboxylate.

40 mg (26%) of sodium salt were obtained from 160 mg (0.38 mmol) of allyl ester. —¹H-NMR (270 MHz, D₂O): δ=1.33 (d, 3H, CH—CH₃); 1.60–1.85 (m, 1H, CH₂—CH₂—CH); 2.20–2.35 (m, 1H, CH₂—CH₂—CH); 2.70–3.00 (m, 2H, CH₂—CH₂—CH); 3.25–3.40 (m, 1H, CH₂—CH₂—CH); 3.48 (dd, 1H, H-6); 3.87 (dd, 1H, H-5); 4.25 (mc, 1H, CH—CH₃); 7.13 (d, 1H, aromatic H); 7.38 (dd, 1H, aromatic H); 8.28 (d, 1H, aromatic H).

EXAMPLE 11

Sodium (1S,5R,6S)-6-[(1R)-1-hydroxyethyl]-(7-chloro-1,2,3,4-tetrahydronaphtho)[2,1-a]carbapen-2-em-3-carboxylate.

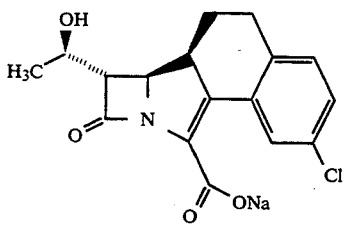

Precursor:

2-Bromo-7-chloro-l-tetralone. 10 g (60 mmol) of 7-chloro-1-tetralone were reacted as described for the precursor in Example 10. The product was obtained in the form of waxy crystals. Yield: 15.4 g (98%). —$^1$H-NMR (270 MHz, CDOl$_3$): δ=2.30–2.60 (m, 2H, CH$_2$—CH$_2$); 2.80–3.00 (m, 1H, CH$_2$—CH$_2$); 3.20–3.40 (m, 1H, CH$_2$—CH$_2$); 4.72 (t, 1H, CHBr); 7.25 (d, 1H, aromatic H); 7.49 (dd, 1H, aromatic H); 8.06 (d, 1H, aromatic H).

Step 1

(3S,4R)-3-[(1R)-1-tert-Butyldimethylsilyloxyethyl]-4-[(2R)-7-chloro-1-oxo-1,2,3,4-tetrahydronaphth-2-yl]-azetidin-2-one.

15.4 g (59 mmol) of 2-bromo-7-chloro-1-tetralone were reacted as described for step 1 in Example 1. After chromatography on silica gel (eluent: toluene/ethyl acetate=5:1), 5.50 g (30%) of product were obtained. —$^1$H-NMR (270 MHz, CDCl$_3$): δ=0.08 and 0.09 (2×s, 6H, SiCH$_3$); 0.86 (s, 9H, SiC(CH$_3$)$_3$); 1.28 (d, 3H, CH—CH$_3$); 1.90–2.15 (m, 1H, CH$_2$—CH$_2$—CH); 2.20–2.38 (m, 1H, CH$_2$—CH$_2$—CH); 2.65–2.80 (m, 1H, CH$_2$—CH$_2$—CH); 3.00–3.18 (m, 3H, CH$_2$—CH$_2$—CH and H-3); 4.26 (mc, 1H, CH—CH$_3$); 4.42 (dd, 1H, H-4); 5.74 (bs, 1H, NH); 7.23 (d, 1H, aromatic H); 7.46 (dd, 1H, aromatic H); 7.98 (d, 1H, aromatic H).

Step 2

Allyl [(3S,4R)-3-[(1R)-1-tert-butyldimethylsilyloxyethyl]-4-[(2R)-7-chloro-1-oxo-1,2,3,4-tetrahydronaphth-2-yl]-2-oxoazetidin-1-yl]-2-oxoaoetate.

Analogously to step 2 in Example 1, 3.8 g (96%) of allyl ester were synthesized from 3.10 g (7.60 mmol) of azetidin-2-one. —$^1$H-NMR (270 MHz, CDCl$_3$): δ=0.06 and 0.08 (2×s, 6H, SiCH$_3$); 0.87 (s, 9H, SiC(CH$_3$)$_3$); 1.20 (d, 3H, CH—CH$_3$); 1.90–2.10 (m, 1H, CH$_2$—CH$_2$—CH); 2.20–2.33 (m, 1H, CH$_2$—CH$_2$—CH); 3.00–3.23 (m, 3H, CH$_2$—CH$_2$—CH); 3.29 (t, 1H, H-3); 4.33 (mc, 1H, CH—CH$_3$); 4.79 (t, 1H, H-4); 4.80 (mc, 2H, CH$_2$—CH=CH$_2$); 5.28–5.50 (m, 2H, CH$_2$—CH=CH$_2$); 5.90–6.10 (m, 1H, CH$_2$—CH=CH$_2$); 7.22 (d, 1H, aromatic H); 7.46 (dd, 1H, H-3); 4.33 (mc, 1H, aromatic H); 8.01 (d, 1H, aromatic H).

Step 3

Allyl (1S,5R,6S)-6-[(1R)-1-tert-butyldimethylsilyloxyethyl]-(7-chloro-1,2,3,4-tetrahydronaphtho)[2,1-a]carbapen-2-em-3-carboxylate.

Cyclization of 3.80 g (7.3 mmol) of allyl ester was carried out as described in Example 1. After 45 minutes at 160° C., the mixture was worked up. After chromatography, 1.50 g (42%) of product were obtained. —$^1$H-NMR (270 MHz, CDCl$_3$): δ=0.10 (s, 6H, SiCH$_3$); 0.90 (s, 9H, SiC(CH$_3$)$_3$); 1.28 (d, 3H, CH—CH$_3$); 1.80–2.15 (m, 2H, CH$_2$—CH$_2$—CH); 2.95–3.08 (m, 2H, CH$_2$—CH$_2$—CH); 3.17 (mc, 1H, CH$_2$—CH$_2$—CH); 3.30 (dd, 1H, H-6); 4.20–4.38 (m, 2H, CH—CH$_3$ and H-5); 4.65–4.95 (m, 2H, CH$_2$—CH=CH$_2$); 5.20–5.50 (m, 2H, CH$_2$CH=CH$_2$); 5.90–6.10 (m, 1H, CH$_2$—CH=CH$_2$); 7.06 (d, 1H, aromatic H); 7.19 (dd, 1H, aromatic H); 7.78 (d, 1H, aromatic H).

Step 4

Allyl (1S,5R,6S)-6-[(1R)-1-hydroxyethyl]-(7-chloro-1,2,3,4-tetrahydronaphtho)[2,1-a]carbapen-2-em-3-carboxylate.

The hydroxyethyl compound was prepared from 1.5 g (3.07 mmol) of silyl ether analogously to step 4 in Example 1. After column chromatography on silica gel, 200 mg (17%) were obtained. —$^1$H-NMR (270 MHz, CDCl$_3$): δ=1.37 (d, 3H, CH—CH$_3$); 1.80–2.00 (m, 1H, CH$_2$—CH$_2$—CH); 2.05–2.20 (m, 1H, CH$_2$—CH$_2$—CH); 2.90–3.10 (m, 2H, CH$_2$—CH$_2$—CH); 3.10–3.28 (m, 1H, CH$_2$—CH$_2$—CH); 3.32 (dd, 1H, H-6); 4.28 (mc, 1H, CH—CH$_3$); 4.35 (dd, 1H, H-5); 4.60–4.95 (m, 2H, CH$_2$—CH=CH$_2$); 5.20–5.50 (m, 2H, CH$_2$—CH=CH$_2$); 5.90–6.10 (m, 1H, CH$_2$—CH=CH$_2$); 7.07 (d, 1H, aromatic H); 7.21(dd, 1H, aromatic H); 7.77 (d, 1H, aromatic H).

Step 5

Sodium (1S,5R,6S)-6-[(1R)-1-hydroxyethyl]-(7-chloro-1,2,3,4-tetrahydronaphtho)[2,1-a]crbapen-2-em-3-carboxylate. 30 mg of sodium salt were obtained from 35 mg (0.094 mmol) of allyl ester. —$^1$H-NMR (270 MHz, D$_2$O): δ=1.31 (d, 3H, CH—CH$_3$); 1.70–1.95 (m, 1H, CH$_2$—CH$_2$—CH); 2.50–2.70 (m, 1H, CH$_2$—CH$_2$—CH); 2.90–3.10 (m, 2H, CH$_2$—CH$_2$—CH); 3.27 (mc, 1H, CH$_2$—CH$_2$—CH); 3.60 (dd, 1H, H-6); 4.29 (mc, 1H, CH—CH$_3$); 4.40 (dd, 1H, H-5); 7.20 (d, 1H, aromatic H); 7.12 (dd, 1H, aromatic H); 7.50 (d, 1H, aromatic H).

EXAMPLE 12

Sodium (1R,5R,6S)-6-[(1R)-1-hydroxyethyl]-(7-chloro-1,2,3,4-tetrahydronaphtho)[2,1-a]carbapen-2-em-3-carboxylate.

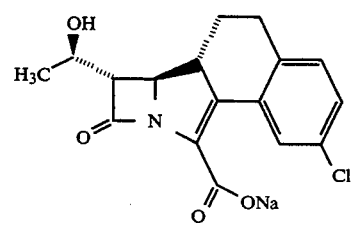

Step 1

(3S,4R)-3-[(1R)-1-tert-butyldimethylsilyloxyethyl]-4-[(2S)-7-chloro-1-oxo-1,2,3,4-tetrahydronaphth-2-yl]-azetidin-2-one.

15.4 g (59 mmol ) of 2-bromo-7-chloro-1-tetralone were reacted as described for step 1 in Example 1. After chromatography on silica gel (eluent: toluene/ethyl acetate=5:1), 6.15 g (34% ) of product were obtained. —$^1$H-NMR (270 MHz, CDCl$_3$): δ=0.08 and 0.10 (2×s, 6H, SiCH$_3$); 1.29 (d, 3H, CH—CH$_3$); 1.77–2.00 (m, 1H, CH$_2$—CH$_2$—CH); 2.20–2.40 (m, 1H, CH$_2$—CH$_2$—CH); 2.47–2.60 (m, 1H, CH$_2$—CH$_2$—CH); 2.85 (mc, 2H, CH$_2$—CH$_2$—CH); 2.98–3.15 (m, 2H, CH$_2$—CH$_2$—CH and H-3); 3.71 (dd, 1H, H-4); 4.20 (mc, 1H, CH—CH₃); 6.42 (bs, 1H, NH); 7.23 (d, 1H, aromatic 7.47 (dd, 1H, aromatic H); 7.96 (d, 1H, aromatic H).

Step 2

Allyl [(3S,4R)-3-[(1R)-1-tert-butyldimethylsilyloxyethyl]-4-[(2S)-7-chloro-1-oxo-1,2,3,4-tetrahydronaphth-2-yl]-2-oxoazetidin-1-yl]-2-oxoacetate.

Analogously to step 2 in Example 1, 4.92 g (59%) of allyl ester were synthesized from 6.5 g (15.9 mmol) of azetidin-2-one. —¹H-NMR (270 MBz, CDCl₃): δ=0.04 and 0.10 (2×s, 6H, SiCH₃); 0.90 (s, 9H, Si((CH₃)₃); 1.29 (d, 3H, CH—CH₃); 1.92-2.10 (m, 1H, CH₂—CH₂—CH); 2.21-2.35 (m, 1H, C₂—CH₂—CH); 3.04 (mc, 2H, C₂—CH₂—CH); 3.18 (mc, 1H, H-3); 3.50 (mc, 1H, CH₂—CH₂—CH); 4.36 (mc, CH—CH₃); 4.81 (mc, 2H, CH₂—CH=CH₂); 5.11 (mc, 1H, H-4); 5.30-5.50 (m, 2H, CH₂—CH=CH₂); 5.90-6.10 (m, 1H, CH₂—CH=CH₂); 7.22 (d, 1H, aromatic H); 7.47 (dd, 1H,. aromatic H); 7.98 (d, 1H, aromatic H).

Step 3

Allyl (1R,5R,6S)-6-[(1R)-1-tert-butyldimethylsilyloxyethyl]-(7-chloro-1,2,3,4-tetrahydronaphtho)[2,1-a]-carbapen-2-em-3-carboxylate.

Cyclization of 4.92 g (9.46 mmol ) of allyl ester was carried out as described in Example 1. After 45 minutes at 160° C., the mixture was worked up. After chromatography, 2.1 g (46%) of product were obtained. —¹H-NMR (270 MHz, CDCl₃): δ=0..10 and 0.11 (2×s, 6H, SiCH₃); 0.92 (s, 9H, SiC(CH₃)₃); 1.29 (d, 3H, CH—CH₃); 1.80-2.00 (m, 1H, CH₂—CH₂—CH); 2.17-2.30 (m, 1H, CH₂—CH₂—CH); 2.90-3.02 (m, 2H, CH₂—CH₂—CH); 3,20 (dd, 1H, H-6); 3.80 (dd, 1H, H-5); 4.23 (mc, 1H, CH—CH₃); 4.78 (mc, 2H, CH₂—CH=CH₂); 5.23-5.56 (m, 2H, CH₂—CH=CH₂); 5.90-6.10 (m, 1H, CH₂—CH=CH₂); 7.10 (d, 1H, aromatic H); 7.25 (dd, 1H, aromatic H); 8.58 (d, 1H, aromatic H).

Step 4

Allyl (1R,5R,6S)-6-[(1R)-1-hydroxyethyl]-(7-chloro-1,2,3,4-tetrahydronaphtho)[2,1-a]carbapen-2-em-3-carboxylate.

The hydroxyethyl compound was prepared from 0.98 mg (2 mmol) of silyl ether analogously to step 4 in Example 1. After column chromatography on ®LiChroprep RP18 (eluent: acetonitrile/water=9:1), 440 mg (59%) were obtained. —¹H-NMR (270 MHz, CDCl₃): δ=1.38 (d, 3H, CH—CH₃); 1.82-1.98 (m, 1H, CH₂—CH₂—CH); 2.22-2.35 (m, 1H, CH₂—CH₂—CH); 2.87-3.02 (m, 2H, CH₂—CH₂—CH); 3.27 (dd, 1H, H-6); 3.28-3.37 (m, 1H, CH₂—CH₂—CH); 3.83 (dd, 1H, H-5); 4.28 (mc, 1H, CH—CH₃); 4.81 (mc, 2H, CH₂—CH=CH₂); 5.20-5.52 (m, 2H, CH₂—CH=CH₂); 5.90-6.12 (m, 1H, CH₂—CH=CH₂); 7.09 (d, 1H, aromatic H); 7.24 (dd, 1H, aromatic H); 8.52 (d, 1H, aromatic H).

Step 5

Sodium (1R,5R,6S)-6-[(1R)-1-hydroxyethyl]-(7-chloro-1,2,3,4-tetrahydronaphtho)[2,1-a]carbapen-2-em-3-carboxylate.

85 mg (44%) of sodium salt were obtained from 200 mg (0.54 mmol) of allyl ester. —¹H-NMR (270 MHz, D₂O): δ=1.32 (d, 3H, CH—CH₃); 1.71 (mc, 1H, CH₂—CH₂—CH), 2.20-2.31 (m, 1H, CH₂—CH₂—CH); 2.82-2.96 (m, 2H, CH₂—CH₂—CH); 3.32 (mc, 1H, CH₂—CH₂—CH); 3.48 (dd, 1H, H-6); 3.85 (dd, 1H, H-5); 4.24 (mc, 1H, CH—CH₃); 7.12-7.28 (m, 2H, aromatic H); 8.08 (d, 1H, aromatic H).

EXAMPLE 13

Sodium (1S, 5R, 6S)-6-[(1R)-1-hydroxyethyl]-(5,7-dimethyl-1,2,3,4-tetrahydronaphtho)[2,1-a]carbapen-2-em-3-carboxylate.

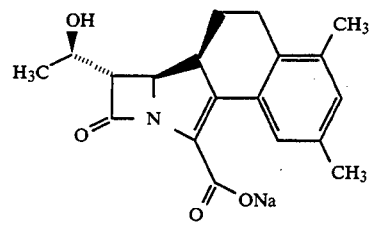

Precursor:
2-Bromo-5,7-dimethyl-1-tetralone.

52 g (298 mmol) of 5,7-dimethyl-1-tetralone were reacted as described for the precursor in Example 10. The product was obtained in crystallized form after trituration in petroleum ether. Yield: 62.2 g (83%). M.p.: 79°-80° C. —¹H-NMR (270 MHz, CDCl₃): δ=2.30 (s, 3H, CH₃); 2.34 (s, 3H, CH₃); 2.43-2.58 (m, 2H, CH₂—CH₂); 2.83 (mc, 1H, CH₂—CH₂); 2.95-3.13 (m, 1H, CH₂—CH₂); 4.70 (t, 1H, CHBr); 7.23 (s, 1H, aromatic H); 7.79 (s, 1H, aromatic H).

Step 1

(3S ,4R)-3-[(1R)-1-tert-butyldimethylsilyloxyethyl]-4-[(2R)-5,7-dimethyl-1-oxo-1,2,3,4-tetrahydronaphth-2-yl]-azetidin-2-one.

8.2 g (32.8 mmol) of 2-bromo-5,7-dimethyl-1-tetralone were reacted as described for step 1 in Example 1. After chromatography on silica gel (eluent: toluene/ethylacetate=5:1), 2.53 g (26%) of product were obtained. —¹H-NMR (270 MHz, CDCl₃): δ=0.90 and 0.91 (2×s; 6H, SiCH₃); 0.97 (s, 9H, SiC(CH₃)₃); 1.28 (d, 3H, CH—CH₃); 1.90-2.15 (m, 1H, CH₂—CH₂—CH); 2.25-2.60 (m, 1H, CH₂—CH₂—CH); 2.29 (s, 3H, CH₃); 2.33 (s, 3H, CH₃); 2.60-2.90 (m, 2H, CH₂—CH₂—CH); 2.95-3.12 (m, 2H, CH₂—CH₂—CH and H-3); 4.24 (mc, 1H, CH—CH₃); 4.40 ( dd, 1H, H-4); 5.72 (bs, 1H, NH); 7.20 (s, 1H, aromatic H); 7.69 (s, 1H, aromatic H).

Step 2

Allyl [(3S,4R)-3-[(1R)-1-tert-butyldimethylsilyloxyethyl]-4-[(2R)-5,7-dimethyl-1-oxo-1,2,3,4-tetrahydronaphth-2-yl]-2-oxoazetidin-1-yl]-2-oxoacetate.

Analogously to step 2 in Example 1, 1.9 g (96%) of allyl ester were synthesized from 1.54 g (3.84 mmol) of azetidin-2-one. —¹H-NMR (270 MHz, CDCl₃): δ=0.04 and 0.06 (2×s, 6H, SiCH₃); 0.87 (s, 9H, SiC(CH₃)₃); 1.19 (d, 3H, CH—CH₃); 1.90-2.10 (m, 1H, CH₂—CH₂CH); 2.20-2.29 (m, 1H, CH₂—CH₂—CH); 2.29 (s, 3H, CH₃); 2.32 (s, 3H, CH₃); 2.70-2.90 (m, 2H, CH₂—CH₂—CH); 3.00-3.27 (m, 2H, CH₂—CH₂—CH); 3.42 (t, 1H, H-3); 4.32 (mc, 1H, CH—CH₃); 4.62 (dd, 1H, H-4); 4.81 (mc, 2H, CH₂—CH=CH₂); 5.25-5.50 (m, 1H, CH₂—CH=CH₂); 5.87-6.10 (m, 1H, CH₂—CH=CH₂); 7.18 (s, 1H, aromatic H); 7.70 (s, 1H, aromatic H).

Step 3

Allyl (1S,5R,6S)-6-[(1R)-1-tert-butyldimethylsilyloxyethyl]-(5,7-dimethyl-1,2,3,4-tetrahydronaphtho)[2,1a]-carbapen-2-em-3-carboxylate.

Cyclization of 1.9 g (3.7 mmol) of allyl ester was carried out as described in Example 1. After 60 minutes at 160° C. the mixture was worked up. After chromatography, 790 mg (44%) of product were obtained. — 1H-NMR (270 MHz, CDCl3): δ=0.10 (s, 6H, SiCH3); 0.90 (s, 6H, SiC(CH3)3); 1.80-2.00 (m, 1H, CH2—CH2—CH); 2.10-2.18 (m, 1H, CH2—CH2—CH); 2.19 (s, 3H, CH3); 2.27 (s, 3H, CH3); 2.64-2.82 (m, 1H, CH2—CH2—CH); 2.92 (mc, 1H, CH2—CH2—CH); 3.09 (mc, 1H, CH2—CH2—CH); 3.27 (dd, 1H, H-6); 4.15-4.35 (mc, 2H, CH—CH3 and H-5); 4.77 (mc, 2H, CH2—CH=CH2); 5.32 (mc, 2H, CH2—CH=CH2); 5.88-6.09 (m, 1H, CH2—CH=CH2); 6.95 (s, 1H, aromatic H); 7.35 (s, 1H, aromatic H).

Step 4

Allyl (1S,5R,6S)-6-[(1R)-1-hydroxyethyl]-(5,7-dimethyl-1,2,3,4-tetrahydronaphtho)[2,1-a]carbapen-2-em-3-carboxylate.

The hydroxyethyl compound was prepared from 790 mg (1.64 mmol) of silyl ether analogously to step 4 in Example 1. After column chromatography on silica gel, 300 mg (50%) were obtained. — 1H-NMR (270 MHz, CDCl3): δ=1.48 (d, 3H, CH—CH3); 1.77-2.00 (m, 2H, CH2—CH2—CH); 2.20 (s, 3H, CH3); 2.28 (s, 3H, CH3); 2.65-2.83 (m, 2H, CH2—CH2—CH); 2.92 (mc, 1H, CH2—CH2—CH); 3.14 (mc, 1H, CH2—CH2—CH); 3.31 (dd, 1H, H-6); 4.20-4.40 (m, 2H, CH—CH3 and H-5); 4.78 (mc, 2H, CH2—CH=CH2); 5.33 (mc, 2H, CH2—CH=CH2); 5.88-6.10 (m, 1H, CH2—CH=CH2); 6.97 (s, 1H, aromatic H).

Step 5

Sodium (1S, 5R, 6S)-6-[(1R)-1-hydroxyethyl]-(5,7-dimethyl-1,2,3,4-tetrahydronaphtho)[2,1-a]carbapen-2-em-3-carboxylate.

60 mg (21%) of sodium salt were obtained from 300 mg (0.41 mmol) of allyl ester. — 1H-NMR (270 MHz, D2O): δ=1.29 (d, 3H, CH—CH3); 1.60-1.82 (m, 2H, CH2—CH2—CH), 2.18 (s, 3H, CH3); 2.22 (s, 3H, CH3); 2.58-2.83 (m, 2H, CH2—CH2CH); 2.90 (mc, 1H, CH2—CH2—CH); 3.06 (dd, 1H, H-6); 4.27 (mc, 1H, CH—CH3); 4.32 (dd, 1H, H-5); 7.00 (s, 1H, aromatic H); 7.12 (s, 1H, aromatic H).

EXAMPLE 14

Potassium (1S,5R,6S)-6-[(1R)-1-hydroxyethyl]-[7-[(4-methylpiperazin-1-yl)-carbonyl]-1,2,3,4-tetrahydronaphtho][2,1-a]carbapen-2-em-3-carboxylate.

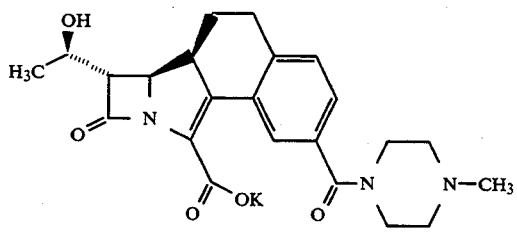

Precursor:

Pentafluorophenyl 1-tetralone-7-carboxylate.

7.3 g (38 mmol) of pentafluorophenol and 8.5 g (41 mmol) of dicyclohexylcarbodiimide were added at 0° C. to a suspension of 6.6 g (35 mmol) of 1-tetralone-7-carboxylic acid in 50 ml of ethyl acetate. After stirring at room temperature for one hour, the urea was filtered off with suction and washed with ethyl acetate, and the solution was concentrated in vacuo. The residue was dissolved using 250 ml of n-heptane and 50 ml of ethyl acetate at boiling heat and treated with active carbon. The active carbon was filtered off at boiling heat. After cooling to 0° C., the product crystallized out. 8.6 g (70%) of the desired ester were obtained by filtering off with suction. M.p. 113° C. — 1H-NMR (270 MHz, CDCl3): δ=2.20 (mc, 2H, CH2—CH2—CH2); 2.75 (t, 2H, CH2—CH2—CH2); 3.09 (t, 2H, CH2—CH2—CH2); 7.47 (d, 1H, aromatic H); 8.26 (dd, 1H, aromatic H); 8.88 (d, 1H, aromatic H).

Step 1

(3S, 4R)-3-[(1R)-1-tert-butyldimethylsilyloxyethyl]-4-[(2R)-1-oxo-7-pentafluorophenoxycarbonyl-1,2,3,4-tetra-hydronaphth-2-yl]-azetidin-2-one.

First 6.0 ml (44 mmol) of triethylamine and then 9.2 ml (51 mmol) of trimethylsilyl triflate were added at 0° C. to a solution of 5.13 g (18 mmol) of azetidinone and 8.23 g (23 mmol) of the pentafluorophenyl ester in 90 ml of anhydrous methylene chloride. The mixture was stirred at room temperature for a further 4 hours, the reaction solution was added to 220 ml of saturated sodium hydrogen carbonate solution, the organic phase was separated off and the aqueous phase was extracted once with 200 ml of ethyl acetate. The combined organic phases were washed with 100 ml of saturated sodium chloride solution, treated with 270 ml of 2N hydrochloric acid and vigorously stirred for 30 minutes. The organic phase was separated off, dried over sodium sulfate and concentrated in vacuo. After chromatography on silica gel (eluent: toluene/ethyl acetate=2:1) and crystallization from n-heptane, 1.21 g (12%) of the desired molar polar diastereomer were obtained. M.p. 149° C. — 1H-NMR (270 MHz, CDCl3): δ=0.1 (s, 6H, SiCH3); 0.89 (s, 9H, SiC(CH3)3); 1.30 (d, 3H, CH—CH3); 2.05-2.20 and 2.30-2.45 (2×m, 2×1H, CH2—CH2—CH); 2.81 (mc, 1H, CH2—CH2—CH); 3.11 (dd, 1H, H-3); 3.15-3.30 (m, 2H, CH2—CH2—CH); 4.28 (mc, 1H, CH—CH3); 4.45 (mc, 1H, H-4); 5.74 (bs, 1H, NH); 7.48 (d, 1H, aromatic H); 8.27 (dd, 1H, aromatic H); 8.82 (d, 1H, aromatic H).

Step 2

Allyl [(3S,4R)-3-[(1R)-1-tert-butyldimethylsilyloxyethyl]-4-[(2R)-1-oxo-7-pentafluorophenoxycarbonyl-1,2,3,4-tetrahydronaphth-2-yl]-2-oxoazetidin-1-yl]-2-oxoacetate.

Analogously to step 2 in Example 1, 2.8 g (98%) of allyl ester were synthesized from 2.4 g (4.1 mmol) of azetidin-2-one. — 1H-NMR (270 MHz, CDCl3): δ=0.08 and 0.10 (2×s, 6H, SiCH3); 0.86 (s, 9H, SiC(CH3)3); 1.27 (d, 3H, CH—CH3); 1.98-2.10 and 2.25-2.40 (2×m, 2×1H, CH2—CH2—CH); 3.15-3.40 (m, 4H, CH2—CH2—CH and H-3); 4.36 (mc, 1H, CH—CH3); 4.72 (dd, 1H, H-4); 4.81 (mc, 2H, CH2—CH=CH2); 5.30-5.50 (m, 2H, CH2—CH=CH2); 5.90-6.05 (m, 1H, CH2—CH=CH2); 7.48 (d, 1H, aromatic H); 8.27 (dd, 1H, aromatic H); 8.89 (d, 1H, aromatic H).

Step 3

Allyl (1S,5R,6S)-6-[(1R)-1-tert-butyldimethylsilyloxyethyl]-(7-pentafluorophenoxycarbonyl-1,2,3,4-tetrahydronaphtho)[2,1-a]carbapen-2-em-3-carboxylate.

Cyclization of 2.4 g (3.45 mmol) of allyl ester was carried out as described in Example 1. After 10 minutes at 140° C., the mixture was worked up. After chromatography, 1.04 g (46%) of product were obtained. — $^1$H-NMR (270 MHz, CDCl$_3$): δ=0.12 (s, 6H, SiCN$_3$); 0.90 (s, 6H, SiC(CH$_3$)$_3$); 1.28 (d, 3H, CH—CH$_3$); 1.80–2.20 (m, 2H, CH$_2$—CH$_2$—CH); 3.05–3.28 (m, 3H, CH$_2$—CH$_2$—CH); 3.31 (dd, 1H, H-6); 4.27 (mc, 1H, CH—CH$_3$); 4.38 (dd, 1H, H-5); 4.77 (mc, 2H, CH$_2$—CH=CH$_2$); 5.28 (mc, 2, CH$_2$—CH=CH$_2$); 5.85–6.05 (m, 1H, CH$_2$—CH=CH$_2$); 7.30 (d, 1H, aromatic H); 8.01 (dd, 1H, aromatic H); 8.55 (d, 1H, aromatic H).

Step 4

Allyl (1S, 5R, 6S)-6-[(1R)-1-tert-butyldimethylsilyloxyethyl]-[7-[(4-methylpiperazin-1-yl)-carbonyl]-1,2,3,4-tetrahydronaphtho][2,1-a]carbapen-2-em-3-carboxylate.

500 mg (0.75 mmol) of pentafluorophenyl ester were dissolved in 3 ml of DMF and 277 μl (2.48 mmol) of N-methylpiperazine were added at −78° C. After a further hour at this temperature, the mixture was added to a mixture of 10 ml of water, 0.9 ml of 2N hydrochloric acid and 7.5 ml of methylene chloride, and the organic phase was separated off, dried over sodium sulfate and concentrated in vacuo. After chromatography of the residue (eluent: methylene chloride/methanol=10:1, then 7:1), 329 mg (75%) of the desired product were obtained. — $^1$H-NMR (270 MHz, CDCl$_3$): δ=0.07 (s, 6H, SiCH$_3$); 0.89 (s, 9H, SiC(CH$_3$)$_3$); 1.26 (d, 3H, CH—CH$_3$); 1.6–2.15 (m, 2H, CH$_2$—CH$_2$—CH); 2.33 (s, 3H, NCH$_3$); 2.3–2.6 (m, 4H, piperazine-CH$_2$); 3.0–3.23 (m, 3H, CH$_2$—CH$_2$—CH); 3.28 (dd, 1H, H-6); 3.4–3.9 (m, 4H, piperazine-CH$_2$); 4.26 (mc, 1H, CH—CH$_3$); 4.33 (dd, 1H, H-5); 4.75 (mc, 2H, CH$_2$—CH=CH$_2$); 5.35 (mc, 2H, CH$_2$—CH=CH$_2$); 5.90–6.10 (m, 1H, CH$_2$—CH=CH$_2$); 7.18 (d, 1H, aromatic H); 7.34 (dd, 1H, aromatic H); 7.78 (d, 1H, aromatic H).

Step 5

Allyl (1S,5R,6S)-6-[(1R)-1-hydroxyethyl]-[7-[(4-methyl-piperazin-1-yl)-carbonyl]-1,2,3,4-tetrahydronaphtho][2,1-a]carbapen-2-em-3-carboxylate.

The hydroxyethyl compound was prepared from 320 mg (0.55 mmol) of silyl ether analogously to step 4 in Example 1. After completion. of the reaction, the mixture was diluted with 30 ml of ethyl acetate and 10 ml of water. The aqueous phase was neutralized with dilute sodium hydrogen carbonate solution and extracted twice with 20 ml of ethyl acetate in each case. After drying over sodium sulfate and concentrating in vacuo, 79 mg (31%) of product were obtained, which was immediately further reacted.

Step 6

Potassium (1S,5R,6S)-6-[(1R)-1-hydroxyethyl]-[7-[(4-methylpiperazin-1-yl)-carbonyl]-1,2,3,4-tetrahydronaphtho][2,1-a]carbapen-2-em-3-carboxylate. 7.6 mg (10%) of potassium salt were obtained from 79 mg (0.17 mmol) of allyl ester. — $^1$H-NMR (270 MHz, D$_2$O): δ=1.29 (d, 3 H, CH—CH$_3$); 1.75–1.95 and 2.08–2.22 (2×m, 2×1H, CH$_2$—CH$_2$—CH); 2.63 (s, 3H, CH$_3$); 2.7–3.2 and 3.5–4.0 (2×m, 11 H, piperazine-CH$_2$, H-6 and CH$_2$—CH$_2$—CH); 3.27 (mc, 1H, CH$_2$—CH$_2$—CH); 4.27 (mc, 1H, CH—CH$_3$); 4.39 (dd, 1H, H-5); 7.30 (mc, 2H, aromatic H); 7.47 (d, 1H, aromatic H).

EXAMPLE 15

Potassium (1R, 5R, 6S)-6-[(1R)-1-hydroxyethyl]-(6-methoxycarbonylchromano)[3,4-a]carbapen-2-em-3-carboxylate.

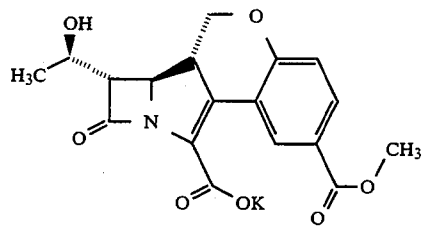

Step 1

(3S ,4R)-3-[(1R)-1-tert-butyldimethylsilyloxyethyl]-4-[(3R)-6-methoxycarbonyl-4-oxochroman-3-yl]-azetidin-2-one.

Starting from 960 mg (3.35 mmol) of (3S, 4R)-4-acetoxy-3-[(1R)-1-tert-butyldimethylsilyloxyethyl]-azetidin-2-one and 1.03 g (5.0 mmol) of methyl 4-oxochroman-6-yl carboxylate, 370 mg (25%) of the less polar diastereomer were obtained after chromatography (eluent: toluene/ethyl acetate=10: 1, 1.11, then 2:1) as described under step 1 in Example 14. — $^1$H-NMR (270 MHz, CDCl$_3$): 6 m 0.08 and 0.10 (2×1s, 2×3H, SiCH$_3$); 0.90 (s, 9H, SiC(CH$_3$)$_3$); 1.28 (d, 3H, CH—CH$_3$); 2.85–2.98 (m, 2H, O—CH$_2$—CH and H-3); 3.72 (dd, 1H, H-4); 3.92 (s, 3H, CO$_2$CH$_3$); 4.18 (mc, 1H, CH—CH$_3$); 4.32 and 4.65 (2×mc, 2×1H, O—CH$_2$—CH); 6.26 (bs, 1H, NH); 7.03 (d, 1H, aromatic H); 8.18 (dd, 1H, aromatic H) 8.59 (d, 1H, aromatic H).

Step 2

Allyl [(3S,4R)-3-[(1R)-1-tert-butyldimethylsilyloxyethyl]-4-[(3R)-6-methoxycarbonyl-4-oxochroman-3-yl)]-2-oxoazetidin-1-yl]-2-oxoacetate.

Analogously to step 2, Example 1, 550 mg (1.25 mmol) of the above (3R)-isomer were reacted with allyl oxalyl chloride. After washing three times with ice-water and drying with MgSO$_4$, the title compound was obtained in quantitative yield as a thick oil, which was immediately cyclized. — $^1$H-NMR (270 MHz, CDCl$_3$): δ=0.02 and 0.08 (2×s, 2×3H, SiCH$_3$); 0.82 (s, 9H, SiC(CH$_3$)$_3$); 1.08 (d, 3H, CH—CH$_3$); 3.2–3.4 (m, 2H, O—CH$_2$CH and H-3); 3.90 (s, 3H, CO$_2$CH$_3$); 4.2–4.5 (m, 4H, H-4, CH—CH3 and O—CH$_2$—CH); 4.77 (mc, 2H, CH$_2$—CH=CH$_2$); 5.35 (mc, 2H, CH$_2$—CH=CH$_2$); 5.95 (mc, 1H, CH$_2$—CH=CH$_2$); 7.02 (mc, 1H, aromatic H); 7.98 (mc, 1H, aromatic H); 8.60 (mc, 1H, aromatic H).

Step 3

Allyl (1R,5R,6S)-6-[(1R)-1-tert-butyldimethylsilyloxyethyl]-(6-methoxycarbonylchromano)-[3,4-a]carbapen-2-em-3-carboxylate.

1.25 mmol of crude product from step 2 were heated under reflux with 600 mg (4.4 mmol) of MeP (OEt)$_2$ in 25 ml of mesitylene for 1 hour. The cold solution was directly chromatographed on silica gel, deactivated with 10% water, using toluene/ethyl acetate (10:1). The title compound was obtained as an oil (160 mg, 25%). —¹H-NMR (270 MHz, CDCl₃): 5–0.11 (s, 6H, SiCH₃); 0.91 (s, 9H, SiC(CH₃)₃); 1.25 (d, 3H, CH—CH₃); 3.25 (dd, 1H, H-6); 3.62–3.70 (m, 1H, O—CH₂CH); 3.77 (dd, 1H, H-5); 3.92 (s, 3H, CO₂CH₃); 4.10–4.20 (m, 1H, O—CH₂—CH); 4.24 (mc, 1H, CH—CH₃); 4.61–4.68 (m, 1H, O—CH₂—CH); 4.72–4.80 (m, 2H, CH₂—CH=CH₂); 5.25–5.50 (m, 2H, CH₂—CH=CH₂); 5.90–6.05 (m, 1H, CH₂—CH=CH₂); 6.90 (d, 1H, aromatic H); 7.94 (dd, 1H, aromatic H); 9.29 (d, 1H, aromatic H).

Step 4

Allyl (1R,5R,6S)-6-[(1R)-1-hydroxyethyl]-(6-methoxycarbonylchromano)-[3,4-a]carbapen-2-em-3-carboxylate.

150 mg (0.29 mmol) of the silyl ether were reacted analogously to step 4, Example 1 (reaction time: 20 h). After chromatography (eluent: toluene/ethyl acetate=1:1), 80 mg (69%) of crystalline product were obtained. —¹-NMR (270 MHz, CDCl₃): δ=1.38 (d, 3H, CH—CH₃); 3.32 (dd, 1H, H-6); 3.62–3.73 (m, 1H, O—CH₂—CH); 3.82 (dd, 1H, H-5); 3.92 (s, 3H, CO₂CH₃); 4.15 (mc, 1H, O—CH₂CH); 4.28 (mc, 1H, CH—CH₃); 4.66–4.95 (m, 3H, O—CH₂Ch and CH₂—CH=CH₂); 5.25–5.50 (m, 2H, CH₂—CH=CH₂); 5.95–6.12 (m, 1H, CH₂—CH=CH₂); 6.92 (d, 1H, aromatic H); 7.96 (dd, 1H, aromatic H); 9.24 (d, 1H, aromatic H).

Step 5

Potassium (1R,5R,6S)-6-[(1R)-1-hydroxyethyl]-(6-methoxycarbonylchromano) [3,4-a]carbapen-2-em-3-carboxylate.

80 mg (0.20 mmol) of allyl ester were reacted analogously to step 5, Example 1. The reaction solution was stirred after 1 h with 3 ml of diethyl ether and 2 ml of water and the water phase was chromatographed on polystyrene absorber resin ®Amberlite XAD-2 (particle size 20–60 mesh) (1.5×15 cm column, in each case 10 ml fractions) using water. The product-containing fractions were freeze-dried and 25 mg (32%) of amorphous solid were obtained. —¹H-NMR (270 MHz, D₂O): δ=1.29 (d, 3H, CH—CH₃); 3.58 (dd, 1H, H-6); 3.69 (mc, 1H, O—CH₂—CH); 3.75 (dd, 1H, H-5); 3.90 (s, 3H, CO₂CH₃); 4.12 (dd, 1H, O—CH₂—CH); 4.27 (mc, 1H, CH—CH₃); 4.65 (dd, 1H, O—CH₂CH); 6.95 (d, 1H, aromatic H); 7.82 (dd, 1H, aromatic H); 8.98 (d, 1H, aromatic H).

EXAMPLE 16

Potassium (1S, 5R, 6S)-6-[(1R)-1-hydroxyethyl]-(7-methoxy-1,2,3,4-tetrahydronaphtho)[2,1-a]carbapen-2-em-3-carboxylate

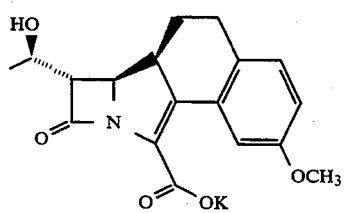

Step 1

(3S, 4R)-3-[(1R)-1-tert-Butyldimethylsilyloxyethyl]-4-(2R)-7-methoxy-1-oxo-1,2,3,4-tetrahydronaphth-2-yl]-azetidin-2-one 2 g (11.4 mmol) of 7-methoxytetralone in 10 ml of THF were added at −78° C. to 8.1 ml of a 1.5 molar solution of lithium diisopropylamide (12.2mmol, in THF/heptane, 6:4) and 60 ml of anhydrous THF After 10 min at −78° C. the mixture is stirred at 0° C. for 30 min. 13.3 ml of a 1 molar solution of chlorotriisopropoxy titanate (13.3 mmol) in hexane were then added dropwise at −78° C., and the mixture was stirred at this temperature for 70 min. After addition of 2.87 g (10 mmol) of (3S,4R)-4-acetoxy-3-[(1R)-1-tert-butyldimethylsilyloxyethyl]-azetidin-2-one, dissolved in 5 ml of THF, the reaction was allowed to warm to 0° C. and the mixture was stirred at this temperature for 30 min. The reaction mixture was poured onto 170 ml of saturated ammonium chloride solution and extracted with ethyl acetate. The organic phase was washed with water, dried over sodium sulfate and concentrated in vacuo. The crude product contains the (1S)- and (1R)-diastereomers in the ratio 3:1. The residue was chromatographed on silica gel (eluent: toluene/ethyl acetate=4:1) and the product crystallized from 120 ml of n-heptane. Yield: 1.28 g (32%), white crystals. —¹H-NMR (270 MHz, CDCl₃): δ=0.09 (s, 6H, Si(CH₃)₂; 0.88 (s, 9H, SiC(CH₃)₃); 1.27 (d, 3H, CHCH₃); 1.95–2.12 and 2.21–2.33 (2×m, 2×1H, CH—CH=CH₂); 2.71 (m, 1H, CH—CH₂—CH₂); 2.98–3.08 (m, 2H, CH—CH₂CH₂); 3.10 (dd, 1H, H-3); 3.84 (s, 3H, OCH₃); 4.26 (m, 1H, CH—CH₃); 4.44 (m, 1H, H-4); 5.75 (br., 1H, NH); 7.09 (dd, 1H, aromatic H); 7.17 (d, 1H, aromatic H); 7.49 (d, 1H, aromatic H).

Step 2

Allyl [(3S,4R)-3-[(1R)-1-tert-butyldimethylsilyloxyethyl]-4-[(2R)-7-methoxy-1-oxo-1,2,3,4-tetrahydronaphth-2-yl )]-2-oxoazetidin-1-yl]-2-oxoacetate Analogously to step 2 in Example 1, 1.1 g (2.27 mmol) of the azetidinone were acylated. The crude product was purified by chromatography on silica gel (eluent: heptane/ethyl acetate=4:1). Yield: 1.15 g (82%). —¹H-NMR (270 MHz, CDCl₃): δ=0.07 and 0.09 (2×s, 2×3H, SiC(CH₃)₃); 0.87 (s, 9H, SiC(CH₃)₃; 1.20 (d, 3H, CH—CH₃); 1.90–2.30 (m, 2H, CH—CH₂—CH₂); 3.00–3.09 (m, 2H, CH—CH₂—CH₂); 3.21 (m, 1H, CH—CH₂—CH₂); 3.29 (m, 1H, H-3); 3.83 (s, 3H, OCH₃); 4.33 (m, 1H, CH—CH₃); 4.67 (m, 1H, H-4); 4.81 (d, 2H, CH₂CH=CH₂); 5.30 and 5.41 (2×d, 2×1H, CH₂—CH=CH₂); 5.98 (m, 1H, CH₂—CH=CH₂); 7.08 (dd, 1H, aromatic H); 7.17 (d, 1H, aromatic H); 7.51 (d, 1H, aromatic H ).

Step 3

Allyl (1S,5R,6S)-6-[(1R)-1-tert-butyldimethylsilyloxyethyl)-(7-methoxy- 1,2,3,4-tetrahydronaphtho)[2,1-a]carbapen-2-em-3-carboxylate Analogously to step 3 in Example 1, 1.13 g (2.2 mmol) of product from step 2 were cyclized in 25 ml of xylene at 140° C. Yield: 370 mg (35%). —¹H-NMR (270 MHz, CDCl₃): δ=0.10 (s, 6H, Si(CH₃)₂); 0.90 (s, 9H, SiC(CH₃)₃); 1.27 (d, 3H, CH—CH₃); 1.80–2.13 (m, 2H, CH—CH₂—CH₂); 2.95–3.04 (m, 2H, CH—CH₂—CH₂); 3.17 (m, 1H, CH—CH₂); 3.28 (dd, 1H, H-6); 3.78 (s, 3H, OCH₃); 420–4.34 (m, 2H, H-5 and CH—CH$_3$); 4.77 (m, 2H, CH$_2$—CH=CH$_2$); 5.25 and 5.41 (2×d, 2×1H, CH$_2$—CH=CH$_2$); 5.99 (m, 1H, CH$_2$—CH=CH$_2$); 6.81 (dd, 1H, aromatic H); 7.03 (d, 1H, aromatic H); 7.40 (d, 1H, aromatic H).

Step 4

Allyl (1S,5R,6S)-6-[(1R)-1-hydroxyethyl]-(7-methoxy-1,2,3,4-tetrahydronaphtho)[2,1-a]carbapen-2-em-3-carboxylate As described for step 4 in Example 1, 369 mg (0.76 mmol) were reacted. The crude product was chromatographed on silica gel (eluent: heptane/ethyl acetate=1:1). Yield: 119 mg (43%). —$^1$H-NMR (270 MHz, CDCl$_3$): δ=1.37 (d, 3H, CH—CH$_3$); 1.81–2.18 (m, 2H, CH—CH$_2$—CH$_2$); 2.92–3.08 (m, 2H, CH—CH$_2$—CH$_2$); 3.21 (m, 1H, CH—CH$_2$—CH$_2$); 3.33 (dd, 1H, H-6); 3.78 (s, 3H, OCH$_3$); 4.20–4.37 (m, 2H, H-5 and CH—CH$_3$); 4.80 (m, 2H, CH$_2$—CH=CH$_2$); 5.26 and 5.41 (2×d, 2×1H, CH$_2$—CH=CH$_2$); 6.00 (m, 1H, CH$_2$—CH=CH$_2$); 6.82 (dd, 1H, aromatic H); 7.03 (d, 1H, aromatic H); 7.41 (d, 1H, aromatic H).

Step 5

Potassium (1S, 5R, 6S)-6-[(1R)-1-hydroxyethyl]-(7-methoxy-1,2,3,4-tetrahydronaphtho)[2,1-a]carbapen-2-em-carboxylate Analogously to step 5 in Example 1, 119 mg (0.33 mmol) were reacted. The crude product was chromatographed on ®LiChroprep RP 18. During the course of this, inorganic salts were removed with water. The product was then eluted with 20% acetonitrile in water. Yield: 45 mg
(3S,4R)-3-[(1R)-1-tert-Butyldimethylsilyloxyethyl]-4( (37%). —$^1$H-NMR (200 MHz, D$_2$O): δ=1.28 (d, 3H, CH—CH$_3$); 1.80 and 2.05 (2×mc, 2×1H, CH$_2$—CH$_2$—CH); 2.85–3.05 (m, 2H, CH$_2$—CH$_2$—CH); 3.21 (mc, 1H, CH$_2$—CH$_2$—CH); 3.55 (dd, 1H, H-6); 3.79 (s, 3H, OCH$_3$); 4.2–4.4 (m, 2H, H-5 and CH—CH$_3$); 6.7–7.2 (m, 3H, aromatic H).

EXAMPLE 17

Sodium (1S, 5R, 6S)-6-[(1R)-1-hydroxyethyl ]-( 7-methoxycarbonyl-1,2,3,4-tetrahydronaphtho[2,1-a]carbapen-2-em-3-carboxylate

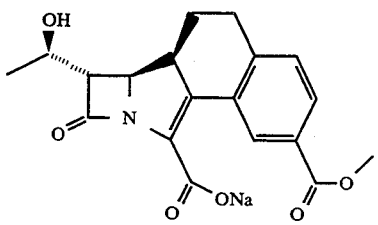

Step 1

(3S ,4R)-3-[(1R)-1-tert-Butyldimethylsilyloxyethyl]-4-[(2R)-7-methoxycarbonyl-1-oxo-1,2,3,4-tetrahydronaphth-2-yl]-azetidin-2-one.

As was described for step 1 in Example 16, 500 mg (2.45 mmol) of methyl 1-tetralone-7-carboxylate were reacted. After chromatography on silica gel (eluent: toluene/ethyl acetate=5:1), 220 mg (23% ) of product were obtained.

$^1$H-NMR (200 MHz, CDCl$_3$): δ=0.09 (s, 6H, SiCH$_3$); 0.85 (s, 9H, SiC(CH$_3$)$_3$); 1.26 (d, 3H, CH—CH$_3$); 1.94–2.20 (m, 1H, CH—CH$_2$—CH$_2$); 2.22–2.40 (m, 1H, CH—CH$_2$CH$_2$); 2.68–2.82 (m, 1H, CH—CH$_2$—CH$_2$); 3.05–3.22 (m, 3H, CH—CH$_2$—CH$_2$ and H-4); 3.95 (s, 3H, COOCH$_3$); 4.26 (mc, 1H, CH—CH$_3$); 4.24 (dd, 1H, H-3); 5.72 (bs, 1H, NH); 7.38 (d, 1H, aromatic H); 8.18 (dd, 1H, aromatic H); 8.65 (.d, 1H, aromatic H).

Step 2

Allyl [(3S,4R)-3-[(1R)-1-tert-butyldimethylsilyloxyethyl]-4-[(2R)-7-methoxycarbonyl-1-oxo-1,2,3,4-tetrahydronaphth-2-yl]-2-oxoazetidin-1-yl]-2-oxoacetate Analogously to step 2 in Example 1, 100 mg (38%) of allyl ester were synthesized from 210 mg (0.49 mmol) of azetidin-2-one. —$^1$H-NMR (270 MHz, CDCl$_3$): δ=0.08 (2×s, 6H, Si(CH$_3$)$_2$; 0.84 (s, 9H, SiC(CH$_3$)$_3$); 1.20 (d, 3H, CH—CH$_3$); 1.90–2.15 (m, 1H, CH—CH$_2$—CH$_2$); 2.20–2.36 (m, CH—CH$_2$—CH$_2$); 3.05–3.28 (mc 3H, CH—CH$_2$—CH$_2$); 3.32 (mc, 1H, H-4); 3.92 (s, 3H, COOCH$_3$); 4.34 (mc, 1H, CH—-CH$_3$); 4.68 (mc, 1H, H-3); 4.81 (mc, 2H, CH$_2$—CH=CH$_2$); 5.25–5.50 (m, 2H, CH$_2$—CH=CH$_2$); 5.88–6.10 (m, 1H, CH$_2$—CH=CH$_2$); 7.36 (d, 1H, aromatic H); 8.16 (dd, 1H, aromatic H); 8.70 (d, 1H, aromatic H).

Step 3

Allyl (1S,5R,6S)-6-[(1R)-1-tert-butyldimethylsilyloxyethyl]-(7-methoxycarbonyl-1,2,3,4-tetrahydronaphtho)[2,1a]-carbapen-2-em-carboxylate.

The cyclization of 880 mg ( 1.62 mmol ) of allyl ester was carried out as described in Example 1. After 15 minutes at 160° C. the mixture was worked up. After chromatography, 550 mg (66% of product) were obtained. —$^1$H-NMR (200 MHz, CDCl$_3$): δ=0.10 (s, 6H, Si(CH$_3$)$_2$); 0.89 (s, 9H, SiC(CH$_3$)$_3$); 1.24 (d, 3H, CH—CH$_3$); 1.80–2.20 (m, 2H, CH—CH$_2$—CH$_2$); 3.30–3.40 (m, 4H, CH—CH$_2$—CH$_2$ and H-5); 3.88 (s, 3H, COOCH$_3$); 4.25 (mc, 1H, CH—CH$_3$); 4.33 (dd, 1H, H-6); 4.78 (mc, 2H, CH$_2$CH=CH$_2$); 5.18–5.50 (m, 2H, CH$_2$—CH=CH$_2$); 5.80–6.20 (m, 1H, CH$_2$—CH=CH$_2$); 7.20 (d, 1H, aromatic H); 7.86 (dd, 1H, aromatic H); 8.40 (d, 1H, aromatic H).

Step 4

Allyl (1S,5R,6S)-6-[(1R)-1-hydroxyethyl]-7-methoxycarbonyl-1,2,3,4-tetrahydronaphtho[2,1-a]carbapen-2-em-3carboxylate.

Analogously to step 4 in Example 1, the hydroxyethyl compound was prepared from 550 mg (1.08 mmol) of silyl ether. After column chromatography on silica gel, 200 mg (47%) were obtained. —$^1$H-NMR (200 MHz, CDCl$_3$): δ=1.38 (d, 3H, CH—CH$_3$); 1.80–2.20 (m, 2H, CH—CH$_2$—CH$_2$); 3.00–3.30 (m, 3H, CH—CH$_2$—CH$_2$); 3.36 (mc, 1H, H-5); 3.90 (s, 3H, COOH$_3$); 4.28 (mc, 1H, CH—CH$_3$); 4.38 (dd, 1H, H-6); 4.80 (mc, 2H, CH$_2$—CH=CH$_2$); 5.20–5.50 (m, 2H, CH$_2$—CH=CH$_2$); 5.80–610 (m, 1H, CH$_2$—CH=CH$_2$); 7.20 (d, 1H, aromatic H); 7.88 (dd, 1H, aromatic H); 8.41 (d, 1H, aromatic H ).

Step 5

Sodium (1S, 5R, 6S)-6-[(1R) -1-hydroxyethyl]-(7-methoxycarbonyl-1,2,3,4-tetrahydronaphtho[2,1-a]carbapen-2-em-3-carboxylate.

45 mg (25%) of sodium salt were obtained from 190 mg (0.48 mmol).

$^1$H-NMR (200 MHz, D$_2$O): δ=1.36 (d, 3H, CH—CH$_3$); 1.60–2.00 (m, 1H, CH—CH$_2$—CH$_2$); 2.10–2.20 (m, 1H, CH—CH$_2$—CH$_2$); 2.95–3.16 (m, 2H, CH—CH$_2$—CH$_2$); 3.25 (mc, 1H, CH—CH$_2$CH$_2$); 3.59

(dd, 1H, H-6); 3.92 (s, 3H, COOCH₃); 4.30 (mc, 1H, CH—CH₃); 4.41 (dd, 1H, H-5); 7.25 (d, 1H, aromatic H); 7.73 (dd, 1H, aromatic H); 7.98 (d, 1H, aromatic H).

EXAMPLE 18

Sodium (1S,5R,6S)-6-[(1R)-1-hydroxyethyl]-(5,6-dimethoxy-1,2,3,4-tetrahydronaphtho)[2,1-a]carbapen-2-em-3-carboxylate.

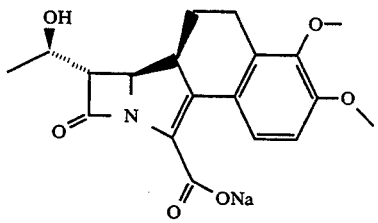

Step 1

(3S,4R)-3-[(1R)-1-tert-Butyldimethylsilyloxyethyl]-4-[(2R)-5,6-dimethoxy-1-oxo-1,2,3,4-tetrahydronaphth-2-yl)-azetidin-2-one.

As was described for step 1 in Example 16, 500 mg (2.42 mmol) of 5,6-dimethoxy-1-tetralone were reacted. After chromatography on silica gel (eluent toluene-/ethyl acetate=5:1), 270 mg (29%) of products were obtained. —¹H-NMR (200 MHz, CDCl₃): δ=0.08 (s, 6H, Si(CH₃)2); 0.85 (s, 9H, Si(CH₃)₃); 1.25 (d, 3H, CH—CH₃); 1.80–2.12 (m, 1H, CH—CH₂—CH₂); 2.20–2.12 (m, 1H, CH—CH₂—CH₂); 2.60–2.95 (m, 2H, CH—CH₂—CH₂); 3.08 (dd, 1H, H-3); 3.28 (mc, 1H, CH—CH₂CH₂); 4.84 (s, 3H, O—CH₃); 4.94 (s, 3H, O—CH₃); 4.27 (mc, 1H, CH—CH₃); 4.42 (dd, 1H, H-4); 5.69 (bs, 1H, NH); 6.91 (d, 1H, aromatic H); 7.82 (d, 1H, aromatic H).

Step 2

Allyl [(3S,4R)-3-[(1R)-1-tert-butyldimethylsilyloxyethyl]-4-[(2R)-5,6-dimethoxy-1-oxo-1,2,3,4-tetrahydronaphth-2-yl)]-2-oxoazetidin-1-yl]-2-oxoacetate.

Analogously to step 2 in Example 1, 910 mg (49%) of allyl ester were synthesized from 1.46 g (3.37 mmol) of azetidin-2-one. —¹H-NMR (200 MHz, CDCl₃): δ=0.05 (s, 3H, Si(CH₃)); 0.06 (s, 3H, Si(CH₃)); 0.84 (s, 9H, SiC(CH₃)₃); 1.18 (d, 3H, CH—CH₃); 1.80–2.10 (m, 1H, CH—CH₂—CH₂); 2.17–2.38 (m, 1H, CH—CH₂—CH₂); 2.70–3.00 (m, 1H, CH—CH₂—CH₂); 3.10–3.40 (m, 3H, CH—CH₂—CH₂ and H-3); 3.84 (s, 3H, O—CH₃); 3.93 (s, 3H, O—CH₃); 4.32 (mc, 1H, CH—CH₃); 4.64 (mc, 1H, H-4); 4.81 (mc, 2H, CH₂—CH=CH₂); 5.20–5.50 (m, 2H, CH₂—CH=CH₂); 5.80–6.10 (m, 1H, CH₂—CH=CH₂); 6.89 (d, 1H, aromatic H); 7.84 (d, 1H, aromatic H).

Step 3

Allyl (1S,5R,6S)-6-[(1R)-1-tert-Butyldimethylsilyloxyethyl]-(5,6-dimethoxy-1,2,3,4-tetrahydronaphtho)[2,1a]carbapen-2-em-3-Carboxylate.

The cyclization of 850 mg (1.56 mmol) of allyl ester was carried out as described in Example 1. After 30 minutes at 160° C. the mixture was worked up. After chromatography, 190 mg (24%) of product were obtained. —¹B-NMR (200 MHz, CDCl₃): δ=0.09 (s, 6H, Si(CH₃)2); 0.88 (s, 9H, SiC(CH₃)₃); 1.28 (d, 3H, CH—CH₃); 1.65–2.00 (m, 1H, CH—CH₂—CH₂); 2.02–2.20 (m, 1H, CH₂—CH₂); 2.70–3.18 (m, 3H, CH—CH-2—CH₂); 3.26 (mc, 1H, H-6); 3.80 (s, 3H, O—CH₃); 3.88 (s, 3H, O—CH₃); 4.18—4.35 (m, 2H, CH—C₃and H-5); 4.78 (mc, 2H, CH₂—CH=CH₂); 5.20–5.50 (m, 2H, CH₂—CH=CH₂); 5.86–6.18 (m, 1H, CH₂—CH=CH₂); 6.78 (d, 1H, aromatic H); 7.64 (d, 1H, aromatic H).

Step 4

Allyl (1S, 5R, 6S)-6-[(1R)-1-hydroxyethyl]-(5,6-dimethoxy-1,2,3,4-tetrahydronaphtho)[2,1-a]carbapen-2-em-3-carboxylate.

Analogously to step 4 in Example 1, the hydroxyethyl compound was prepared from 180 mg (0.35 mmol) of silyl ether. After column chromatography on silica gel, 55 mg (39%) were obtained. —¹H-NMR (200 MHz, CDCl₃): 6–1.39 (d, 3H, CH—CH₃); 1.80–2.00 (m, 1H, CH—CH₂—CH₂); 2.08–2.30 (m, 1H, CH—CH-2—CH₂); 2.75–3.00 (m, 1H, CH—CH₂—CH₂); 3.05–3.28 (m, 2H, CH—CH₂—CH₂); 3.34 (dd, 1H, H-6); 3.80 (s, 3H, OCH₃); 3.85 (s, 3H, OCH₃); 4.20–4.40 (m, 2H, CH—CH₃ and H-5); 4.60–4.92 (m, 2H, CH₂—CH=CH₂); 5.20–5.50 (m, CH₂—CH=CH₂); 5.90–6.15 (m, 1H, CH₂—CH=CH₂); 6.80 (d, 1H, aromatic H); 7.65 (d, 1H, aromatic H).

Step 5

Sodium (1S,5R,6S)-6-[(1R)-1-hydroxyethyl]-(5,6-dimethoxy-1,2,3,4-tetrahydronaphtho)[2,1-a]carbapen-2-em-3-carboxylate.

40 mg (84%) of sodium salt were obtained from 50 mg (0.125 mmol).

¹H-NMR (200 MHz, D₂O): δ=1.34 (d, 3H, CH—CH₃); 1.40–1.70 (m, 1H, CH—CH₂—CH₂); 2.10–2.30 (m, 1H, CH—CH₂—CH₂); 2.82 (mc, 1H, CH—CH₂—CH₂); 3.00–3.24 (m, 2H, CH—CH-2—CH₂); 3.56 (dd, 1H, H-6); 3.80 (s, 3H, OCB₃); 3.90 (s, 3H, OCB₃); 4.28 (mc, 1H, CH—CH₃); 4.36 (dd, 1H, H-5); 6.94 (d, 1H, aromatic H); 7.32 (d, 1H, aromatic H).

EXAMPLE 19

Pivaloyloxymethyl (1S,5R,6S)-6-[(1R)-1-hydroxyethyl]-(1,2,3,4-tetrahydronaphtho)[2,1-a]carbapen-2-em-3-carboxylate.

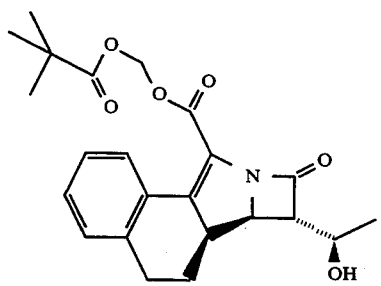

18 mg (0.12 mmol) of chloromethyl pivaloate were dissolved in 2 ml of dry DMF and 12 mg (0.12 mmol) of sodium bromide were added. After 48 hours at room temperature, the mixture was filtered through glass wadding and 20 mg (0.06 mmol) of potassium (1S,5R,6S)-6-[(1R)-1-hydroxyethyl]-(1,2,3,4-tetrahydronaphtho)[2,1-a]carbapen-2-em-3-carboxylate (Example 1) were added to the filtrate and the mixture was stirred at room temperature for a further 4 hours. It was taken up in 10 ml of water and 70 ml of diethyl ether.

The organic phase was washed with 10 ml each of 9% strength sodium bicarbonate solution and 25% strength ammonium chloride solution and 3×10 ml of water. It was dried over magnesium sulfate, concentrated and dried to constant weight by the oil pump. 20 mg (81%) of the title compound are obtained. —$^1$H-NMR (200 MHz, CDCl$_3$): δ=1.24 (s, 9H, C(CH$_3$)$_3$); 1.36 (d, 3H, CH—CH$_3$); 1.80–2.20 and 2.80–3.30 (2×m, 5H, CH$_2$—CH$_2$—CH); 3.34 (dd, 1H, H-6); 4.32 (mc, 1H, CH—CH$_3$); 4.36 (dd, 1H, H-5); 5.91 (mc, 2H, O—CH$_2$—O); 7.00–7.30 (m, 3H, aromatic H); 7.72 (d, 1H, aromatic H).

EXAMPLE 20

[1-(Pivaloyloxy)ethyl]-(1S, 5R, 6S)-6-[(1R)-1-hydroxyethyl]-(1,2,3,4-tetrahydronaphtho)[2,1-a]carbapen-2-em-3-carboxylate.

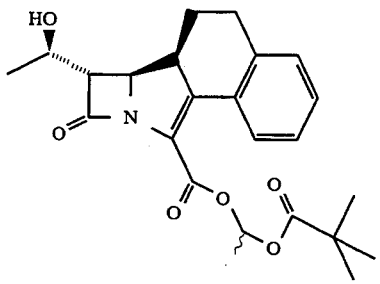

As described in Example 19, 100 mg (0.3 mmol) of potassium salt (Example 1) were reacted with 125 mg (0.6 mmol) of 1-bromoethyl pivaloate. After chromatography on silica gel (eluent: ethyl acetate/n-heptane=3:1), the product could be obtained as an oil. Yield: 50 mg (39%). —$^1$H-NMR (200 MHz, CDCl$_3$): δ=1.21 and 1.23 (2×s, 9H, C(CH$_3$)$_3$); 1.36 (d, 3H, CH—CH$_3$); 1.53 and 1.57 (2×d, 3H, OCH(CH$_3$)O); 1.75–2.25 (m, 2H, CH—CH$_2$—CH$_2$); 3.02–3.15 (m, 2H, CH—CH$_2$); 3.25 (mc, 1H, CH—CH$_2$—CH$_2$); 3.34 (dd, 1H, H-6); 4.20–4.40 (m, 2H, H-6 and CHCH$_3$); 6.80–7.35 and 7.73–7.82 (2×m, 5H, OCH(CH$_3$)O and aromatic H).

EXAMPLE 21

(1S, 5R, 6S)-6-[(1R)-1-Hydroxyethyl]-[7-[(4,4-dimethyl-piperazinium-1-yl)-carbonyl]-1,2,3,4-tetrahydronaphtho][2,1-a]carbapen-2-em-3-carboxylate

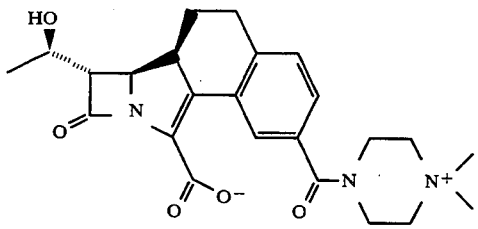

Starting from 475 mg (0.82 mmol) of step 4 in Example 14, the hydroxyethyl compound was prepared there as described in step 5. The crude product was alkylated with 215 μl (3.2 mmol) of iodomethane in 10 ml of dichloromethane. After 24 h at room temperature, the mixture was concentrated in vacuo and the crude product was further reacted as described for step 5 in Example 1. After chromatography on ®LiChroprep RP 18 and lyophilization, 37.9 mg (11%) of the desired product were obtained. —$^1$H-NMR (270 MHz, D$_2$O): δ=1.30 (d, 3H, CH—CH$_3$); 1.75–1.95 and 2.1–2.25 (2×m, 2×1H, CH—CH$_2$—CH$_2$); 3.03–3.15 (m, 2H, CH—CH$_2$—CH$_2$); 3.28 (s, 6H, N(CH$_3$)$_2$); 3.3–4.2 (m, 10H, piperazine-CH$_2$, H-6, CH—CH$_2$—CH$_2$); 4.27 (mc, 1H, CH—CH$_3$); 4.39 (dd, 1H, H-5); 7.33 (mc, 2H, aromatic H); 7.49 ( d, 1H, aromatic H ).

EXAMPLE 22

Potassium (1S,5R,6S)-6-[(1R)-1-hydroxyethyl]-[7-[(morpholin-4-yl)-carbonyl]-1,2,3,4-tetrahydronaphtho][2,1-a]carbapen-2-em-3-carboxylate

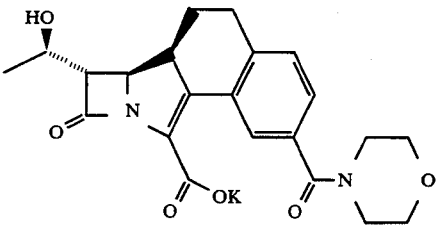

Step 1

Allyl (1S,5R,6S)-6-[(1R)-1-tert-butyldimethylsilyloxyethyl]-[7-[(morpholin-4-yl)-carbonyl]-1,2,3,4-tetrahydronaphtho][2,1-a]carbapen-2-em-3-carboxylate.

Analogously to step 4 in Example 14, 500 mg (0.75 mmol) of pentafluorophenyl ester are reacted with 215 μl (2.48 mmol) of morpholine. After chromatography (eluent:toluene/ethyl acetate=1:1), 251 mg (59%) of the desired product were obtained. —$^1$H-NMR (200 MHz, CDCl$_3$): δ=0.09 (s, 6H, SiCH$_3$); 0.89 (s, 9H, SiC(CH$_3$)$_3$); 1.27 (d, 3H, CH—CH$_3$); 1.8–2.15 (m, 2H, CH$_2$—CH$_2$—CH); 3.0–3.3 (m, 4H, CH$_2$—CH$_2$—CH and H-6); 3.4–3.9 (m, 8H, morpholine-CH$_2$); 4.18–4.38 (m, 2H, CH—CH$_3$ and H-5); 4.76 (mc, 2H, CH$_2$—CH=CH$_2$); 5.34 (mc, 2H, CH$_2$—CH=CH$_2$); 5.85–6.10 (m, 1H, CH$_2$—CH—CH$_2$); 7.10–7.40 (m, 2H, aromatic H); 7.78 (d, 1H, aromatic H).

Step 2

Allyl (1S,5R,6S)-6-[(1R)-1-hydroxyethyl ]-[7-[(morpholin-4-yl) -carbonyl]-1,2,3,4-tetrahydronaphtho][2,1-a]carbapen-2-em-3-carboxylate 237 mg (0.42 mmol) of silyl ether were reacted analogously to step 5 in Example 14. After chromatography on ®LiChroprep RP 18 (eluent: water/acetonitrile gradient), 77 mg (41%) of the product were obtained. —$^1$H-NMR (200 MHz, CDCl$_3$): δ=1.37 (d, 3H, CH—CH$_3$); 1.75–2.20 (m, 2H, CH$_2$—CH$_2$—CH); 2.90–3.15 (m, 3H, CH$_2$—CH$_2$—CH); 3.29 (dd, 1H, H-6); 3.4–3.9 (m, 8H, morpholine-CH$_2$); 4.18–4.35 (m, 2H, CH—CH$_3$ and H-5); 5.77 (mc, 2H, CH$_2$—CH—CH$_2$); 5.22–5.50 (m, 2H, CH$_2$—CH=CH$_2$); 5.88–6.10 (m, 1H, CH$_2$—CH=CH$_2$); 7.15–7.40 (m, 2H, aromatic H); 7.82 (d, 1H, aromatic H).

Step 3

Potassium (1S,5R,6S)-6-[(1R)-1-hydroxyethyl]-[7-[(morpholin-4-yl) -carbonyl]-1,2,3,4-tetrahydronaphtho]-[2,1-a]carbapen-2-em-3-carboxylate Analogously to step 5 in Example 1, 73 mg (0.16 mmol) of amide were reacted with 35.7 mg (0.194 mmol) of potassium-2-ethylhexanoate and 15 μl (=0.097 mmol) of 2-ethylhexanoic acid. After chromatography on ®LiChroprep RP 18 (eluent: water-/acetonitrile, gradient of water to water/acetonitrile=9:1), 35 mg (48%) of potassium salt were obtained. —¹H-NMR (200 MHz, D₂O): δ=1.35 (d, 3H, CH—CH₃); 1.75-2.05 and 2.10-2.30 (2×m, 2×1H, CH₂—CH₂—CH); 3.00-3.18 (m, 2H, CH₂—CH₂—CH); 3.32 (mc, 1H, CH₂—CH₂—CH); 3.45-4.02 (m, 9H, morpholine-CH₂ and H-6); 4.33 (mc, 1H, CH—CH₃); 4.45 (dd, 1H, H-5); 7.32 (mc, 2H, aromatic H); 7.50 (d, 1H, aromatic H).

EXAMPLE 23

Sodium (1S,5R,6S)-6-[(1R)-1-hydroxyethyl]-(6,7-dimethoxy-1,2,3,4-tetrahydronaphtho)[2,1-a]carbapen-2-em-carboxylate

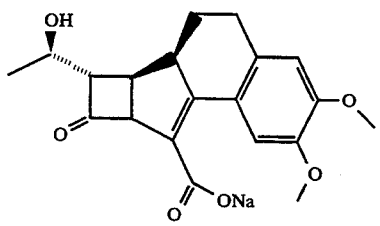

Step 1

(3S, 4R)-2-[(1R)-1-tert-Butyldimethylsilyloxyethyl]-4-[(2R)-6,7-dimethoxy-1-oxo-1,2,3,4-tetrahydronaphth-2-yl]-azetidin-2-one.

As was described for step 1 in Example 16, 4.0 g (19.4 mmol) of 6,7-dimethoxy-1-tetralone were reacted. After chromatography on silica gel (eluent toluene/ethyl acetate=3:1), 1.3 g (32%) of product were obtained. —¹H-NMR (200 MHz, CDCl₃): δ=0.09 (s, 6H, Si(CH₃)₂); 0.85 (s, 9H, SiC(CH₃)₃); 1.24 (d, 3H, CH—CH₃); 1.90-2.10 (m, 1H, CH—CH₂—CH₂); 2.20-2.40 (m, 1H, CH—CH₂—CH₂); 2.60-2.78 (m, 1H, CH—CH₂—CH₂); 2.90-3.20 (m, 3H, CH—CH₂—CH₂ and H-3); 3.90 (s, 3H, OCH₃); 3.94 (s, 3H, OCH₃); 2.23 (mc, 1H, CH—CH₃); 4.44 (dd, 1H, H-4); 5.72 (bs, 1H, NH); 6.65 (s, 1H, aromatic H ).

Step 2

Allyl [(3S,4R)-3-[(1R)-1-tert-butyldimethylsilyloxyethyl]-4-[(2R)-6,7-dimethoxy-1-oxo-1,2,3,4-tetrahydronaphth-2-yl]-2-oxoazetidin-1-yl]-2-oxoacetate Analogously to step 2 in Example 1, 2.35 g (77%) of allyl ester was synthesized from 2.43 g (5.6 mmol) of azetidin-2-one. —¹H-NMR (200 MHz, CDCl₃): δ=0.05 (s, 3H, Si(CH₃)); 0.07 (s, 3H, Si(CH₃)); 0.83 (s, 9H, SiC(CH₃)₃); 1.18 (d, 3H, CH—CH₃); 1.90-2.14 (m, 1H, CH—CH₂—CH₂); 2.15-2.38 (m, 1H, CH—CH₂—CH₂); 2.90-3.40 (m, 4H, CH—CH₂—CH₂ and H-3); 3.89 (s, 3H, OCH₃); 3.92 (s, 3H, OCH₃); 4.32 (mc, 1H, CH—CH₃); 4.64 (mc, 1H, H-4); 4.81 (mc, 2H, CH₂—CH=CH₂); 5.25-5.52 (m, 2H, CH₂—CH=CH₂); 5.80-6.20 (m, 1H, CH₂—CH=CH₂); 6.65 (s, 1H, aromatic H); 7.50 (s, 1H, aromatic H).

Step 3

Allyl (1S,5R,6S)-6-[(1R)-1-tert-butyldimethylsilyloxyethyl]-(6,7-dimethoxy-1,2,3,4-tetrahydronaphtho)[2,1-a]carbapen-2-em-3-carboxylate The cyclization of 2.35 g (4.6 mmol) of allyl ester was carried out as described in Example 1. After 20 minutes at 160° C. the mixture was worked up. After chromatography, 230 mg (16%) of product were obtained. —¹H-NMR (200 MHz, CDCl₃): δ=0.09 (s, 6H, Si(CB₃)₃); 0.91 (s, 9H, SiC(CH₃)₃); 1.23 (d, 3H, CH—CH₃); 1.80-2.20 (m, 2H, CH—CH₂—CH₂); 2.90-3.20 (m, 3H, CH—CH₂CH₂); 3.26 (dd, 1H, H-3); 3.83 (s, 3H, OCH₃); 3.84 (s, 3H, OCH₃); 4.20-4.36 (m, 2H, CH—CH₃ and H-4); 4.78 (m, 2H, C₂—CH=CH₂); 5.20-5.53 (m, 2H, CH₂—CH=CH₂); 5.83-6.13 (m, 1H, CH₂—CH=CH₂); 6.59 (s, 1H, aromatic H); 7.58 (s, 1H, aromatic H).

Step 4

Allyl (1S,5R,6S)-6-[(1R)-1-hydroxyethyl](6,7-dimethoxy-1,2,3,4-tetrahydronaphtho)[2,1-a]carbapen-2-em-3-carboxylate Analogously to step 4 in Example 1, the hydroxyethyl compound was prepared from 375 mg (0.73 mmol ) of silyl ether. After column chromatography on silica gel, 100 mg (34%) were obtained. —¹H-NMR (200 MHz, CDCl₃): δ=1.38 (d, 3H, CH—CH₃); 1.60-2.20 (m, 2H, CH—CH₂—CH₂); 2.30-3.22 (m, 3H, CH—CH₂—CH₂); 3.32 (dd, 1H, H-6); 3.86 (s, 6H, OCH₃); 4.20-4.40 (m, 2H, CH—CH₃ and H-5); 4.60-4.95 (m, 2H, CH₂—CH=CH₂); 5.20-5.58 (m, 2H, CH₂—CH=CH₂); 5.88-6.18 (m, 1H, CH₂—CH=CH₂); 6.60 (s, 1H, aromatic H); 7.59 ( s, 1H, aromatic H).

Step 5

Sodium (1S,5R,6S)-[(1R)-1-hydroxyethyl](6,7-dimethoxy-1,2,3,4-tetrahydronaphtho)[2,1-a]carbapen-2-em-3-carboxylate 12 mg (14%) of sodium salt were obtained from 90 mg (0.225 mmol) of allyl ester. —¹H-NMR (200 MHz, D₂O): δ=1.34 (d, 3H, CH—CH₃); 1.60-1.90 (m, 1H, CH—CH₂—CH₂); 2.02-2.20 (m, 1H, CH—CH₂—CH₂); 2.90-3.10 (m, 2H, CH—CH₂—CH₂); 3.10-3.30 (m, 1H, CH—CH₂—CH₂); 3.58 (dd, 1H, H-6); 3.82 (s, 3H, OCH₃); 3.86 (s, 3H, OCH₃); 4.20-4.40 (m, 2H, CH—CH₃ and H-5); 6.86 (s, 1H, aromatic H) ; 7.24 (s, 1H, aromatic H).

EXAMPLE 24

Potassium (1S,5R,6S)-6-[(1R)-1-hydroxyethyl]-(5-fluoro-1,2,3,4-tetrahydronaphtho)[2,1-a]carbapen-2-em-carboxylate

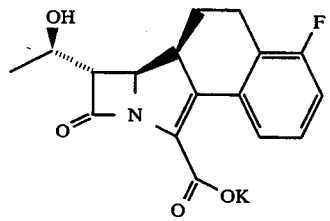

Step 1

(3S, 4R)-3-[(1R)]-1-tert-Butyldimethylsilyloxyethyl]-4-[( 2R)-5-fluoro-1-oxo-1,2,3,4-tetrahydronaphth-2-yl]-azetidin-2-one As was described for step 1 in Example 16, 15 ml of a 1.5 molar solution of lithium diisopropylamide tetrahydrofuran complex (22.5 mmol in cyclohexane) were added at −78° C. to a solution of 3.28 g (20.0 mmol) of 5-fluoro-1-tetralone in 100 ml of THF. The mixture was stirred at −78° C. for 10 min and at 0° C. for 30 min. 24 ml of a 1 molar solution of chlorotriisopropoxy titanate (24 mmol) in hexane were then added dropwise at −78° C. and the mixture was stirred at this temperature for 70 min. After addition of 5.75 g (20 mmol) of (3S,4R)-4-acetoxy-3-[(1R)]-1-tert-butyldimethylsilyloxyethyl]-azetidin-2-one, dissolved in 10 ml of THF, the reaction was allowed to warm to 0° C. and was stirred at this temperature for 30 min. The reaction mixture was poured onto 170 ml of saturated ammonium chloride solution and extracted with ethyl acetate. The organic phase was washed with water, dried over sodium sulfate and concentrated in vacuo. The crude product contained the (1S)- and (1R)-diastereomers in a ratio of 2:1. The residue was chromatographed on silica gel (eluent: toluene/ethyl acetate=6:1) and the product was chromatographed on ®LiChroprep RP 18 (eluent: acetonitrile/water=3:1) to separate the diastereomers. Yield: 1.05 g (13%), white crystals. —$^1$H-NMR (270 MHz, CDCl$_3$): δ=0.09 (s, 6H, Si(CH$_3$)$_2$); 0.88 (s, 9H, SiC(CH$_3$)$_3$); 1.24 (d, 3H, CH—CH$_3$); 1.99-2.17 (2×m, 2H, CH—CH$_2$—CH$_2$); 2.70-3.01 (m, 3H, CH—CH$_2$—CH$_2$); 3.08 (dd, 1H, H-3); 4.21 (m, 1H, CH—CH$_3$); 4.42 (m, 1H, H-4); 5.78 (bs, 1H, NH); 7.20-7.41 (m, 2H, aromatic H); 7.82 (m, 1H, aromatic H).

Step 2

Allyl [(3S,4R)-3-[(1R)]-1-tert-butyldimethylsilyloxyethyl]-4-[(2R)-5-fluoro-1-oxo-1,2,3,4-tetrahydronaphth-2-yl]-2-oxoazetidin-1-yl]-2-oxoacetate Analogously to step 2 in Example 1, 0.95 g (2.42 mmol) of the azetidinone was acylated. The crude product was purified by stirring with pentane (15 ml). Yield: 0.55 g (46%). —$^1$H-NMR (270 MHz, CDCl$_3$): δ=0.06 and 0.08 (2×s, 2×3H, Si(CH$_3$)$_2$); 0.84 (s, 9H, SiC(CH$_3$)$_3$); 1.19 (d, 3H, CH—CH$_3$); 1.90-2.40 (m, 2H, CH—CH$_2$—CH$_2$); 2.80-3.00 (m, 1H, CH—CH$_2$—CH$_2$); 3.18-3.39 (m, 3H, CH—CH$_2$—CH$_2$ and H-3); 4.36 (m, 1H, H-4); 4.80 (d, 2H, CH$_2$—CH=CH$_2$); 5.32 and 5.40 (2×d, 2×1H, CH$_2$—CH=CH$_2$); 5.98 (m, 1H, CH$_2$—CH=CH$_2$); 7.20-7.40 (m, 2H, aromatic H); 7.84 (dd, 1H, aromatic H).

Step 3

Allyl (1S,5R,6S)-6-[(1R)-1-tert-butyldimethylsilyloxyethyl]-(5-fluoro-1,2,3,4-tetrahydronaphtho)[2,1-a]carbapen-2-em-carboxylate Analogously to step 3 in Example 1, 0.55 g (1.09 mmol) of product from step 2 was cyclized in 20 ml of mesitylene at 160° C. After 45 min at this temperature the mixture was worked up and the crude product was chromatographed (eluent: toluene/ethyl acetate=50:1). Yield: 460 mg (89%). —$^1$H-NMR (270 MHz, CDCl$_3$): δ=0.10 (s, 6H, Si(CH$_3$)$_2$); 0.90 (s, 9H, SiC(CH$_3$)$_3$); 1.27 (d, 3H, CH—CH$_3$); 1.80-2.13 (m, 2H, CH—CH$_2$—CH$_2$); 2.95-3.04 (m, 2H, CH—CH$_2$—CH$_2$); 3.17 (m, 1H, CH—CH$_2$—CH$_2$); 3.28 (dd, 1H, H-6); 4.20-4.34 (m, 2H, H-5 and CH—CH$_3$); 4.77 (m, 2H, CH$_2$—CH=CH$_2$); 5.25 and 5.41 (2×s, 2×1H, CH$_2$—CH=CH$_2$); 5.99 (m, 1H, CH$_2$—CH=CH$_2$); 6.81 (dd, 1H, aromatic H); 7.03 (d, 1H, aromatic H); 7.40 (d, 1H, aromatic H).

Step 4

Allyl (1S,5R,6S)-6-[(1R)-1-hydroxyethyl]-(5-fluoro-1,2,3,4-tetrahydronaphtho)[2,1-a]carbapen-2-em-3-carboxylate As described for step 4 in Example 1, 450 mg (0.95 mmol) were reacted. The crude product was chromatographed on silica gel (eluent: toluene/ethyl acetate=1:1). Yield: 240 mg (71%). The substance was immediately further reacted.

Step 5

Potassium (1S,5R,6S)-6-[(1R)-1-hydroxyethyl]-(5-fluoro-1,2,3,4-tetrahydronaphtho)[2,1-a]carbapen-2-em-3-carboxylate Analogously to step 5 in Example 1, 240 mg (0.67 mmol) were reacted. The crude product was chromatographed on ®LiChroprep RP 18 (eluent: water). Yield: 57 mg (24%). —$^1$H-NMR (200 MHz, D$_2$O): δ=1.28 (d, 3H, CH—CH$_3$); 1.71-1.96 and 2.17-2.30 (2×m, 2×1H, CH$_2$—CH$_2$—CH); 2.85-2.98 (m, 1H, CH$_2$—CH$_2$—CH); 3.07-3.38 (m, 2H, CH$_2$—CH$_2$—CH); 3.61 (dd, 1H, H-6); 4.23-4.38 (m, 1H, CH—CH$_3$); 4.42 (dd, 1H, H-5); 6.97-7.37 (m, 3H, aromatic H).

EXAMPLE 25

Pivaloyloxymethyl (1S,5R,6S)-6-[(1R)-1-hydroxyethyl](thiochromano)-[1,2-c]carbapen-2-em-3-carboxylate

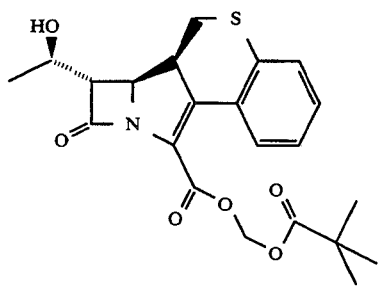

As described in Example 19, 12 mg (0.12 mmol) of sodium bromide were added to 18 mg (0.12 mmol) of chloromethyl pivaloate and the mixture was then reacted with 18 mg (0.05 mmol) of potassium (1S,5R,6S)-6-[(1R)-1-hydroxyethyl]-(thiochromano)[1,2-c]carbapen-2-em-3-carboxylate (Example 8). 15 mg (81%) of the title compound were obtained. —$^1$H-NMR (200 MHz, CDCl$_3$): δ=1.25 (s, 9H, C(CH$_3$)$_3$); 1.36 (d, 3H, CH—CH$_3$); 3.00-3.45 (m, 4H, S—CH$_2$—CH and H-6); 4.36 (mc, 1H, CH—CH$_3$); 4.41 (dd, 1H, H-5); 5.91 (mc, 2H, OCH$_2$); 6.98-7.27 (m, 3H, aromatic H); 7.50 (d, 1H, aromatic H).

EXAMPLE 26

Potassium (1S,5R,6S)-6-[1 R)-1-hydroxyethyl](11,2,3,4-tetrahydronaphthl)[2,1-a]carbapen-2-em-3-carboxylate Step 1

(3S, 4R)-3-[(1R)-1-Hydroxyetyl]-4-[(2R)-1-oxo-1,2,3,4-tetrahydronaphth-2-yl]-azetidin-2-one 1.6 g (4.3 mmol) of step 1 from Example 1 were dissolved in 8.5 ml of acetonitrile and 0.96 ml of boron trifluoride etherate was added at 0° C. After 15 minutes at 0° C. the reaction was complete and 10 ml each of ethyl acetate and water were added. The pH was adjusted to 7.0 and the aqueous phase was extracted again with ethyl acetate. After drying over magnesium sulfate, the extract was concentrated to dryness in vacuo. Yield: 805 mg (73%) of an oil, which became solid on standing in a refrigerator. —$^1$H-NMR (200 MHz, CDCl$_3$): δ=1.40 (d, 3H, CH—CH$_3$); 1.85–2.08 and 2.19–2.36 (2×m, 2H, CH—CH$_2$—CH$_2$); 2.73 (mc, 1H, CH—CH$_2$—CH$_2$); 3.03–3.18 (m, 3H, H-3 and CH—CH$_2$—CH$_2$); 3.85 (dd, 1H, H-4); 4.20 (mc, 1H, CH—CH$_3$); 4.45 (bs, 1H, OH); 6.17 (bs, 1H, NH); 7.25–7.38 and 7.48–7.59 (2×m, 3H, aromatic H); 8.02 (dd, 1H, aromatic H).

Step 2

(3S ,4R)-3-[(1R)-1-Triethylsilyloxyethyl]-4-[(2R)-1-oxo-1,2,3,4-tetrahydronaphth-2-yl]-azetidin-2-one 0.06 ml of pyridine and 0.1 ml of triethylchlorosilane were added successively at 0° C. to 100 mg (0.39 mmol) of the hydroxyethyl compound from step 1 in 3 ml of anhydrous methylene chloride and then stirred at room temperature for 3 h. The reaction mixture was diluted with 10 ml of methylene chloride and washed successively with dilute hydrochloric acid, saturated NaHCO$_3$ solution and water. After drying over sodium sulfate and concentration in vacuo, the residue was chromatographed on silica gel (eluent: toluene/ethyl acetate=1:2). Yield: 122 mg (85%). —$^1$H-NMR (200 MHz, CDCl$_3$): δ=0.50–0.70 (2×m, 6H and 9H, SiCH$_3$CH$_3$); 1.28 (d, 3H, CH—CH$_3$); 1.95–2.38 (m, 2H, CH—CH$_2$—CH$_2$); 2.76 (dt, 1H, CH—CH$_2$—CH$_2$) 3.02–3.16 (m, 3H, CH—CH$_2$—CH$_2$ and H-3); 4.23 (mc, 1H, CH—CH$_3$); 4.43 (dd, 1H, H-4); 5.8 (bs, 1H, NH); 7.22–7.38 and 7.45–7.57 (2×m, 3H, aromatic H); 8.02 (dd, 1H, aromatic H).

The further reactions were carried out as described in Example 3.

EXAMPLE 27

[1-(Ethoxycarbonyloxy)ethyl (1S,5R,6S)-6-[(1R)-1-hydroxyethyl]-(1,2,3,4-tetrahydronaphtho)[2,1-a]carbapen-2-em-3-carboxylate

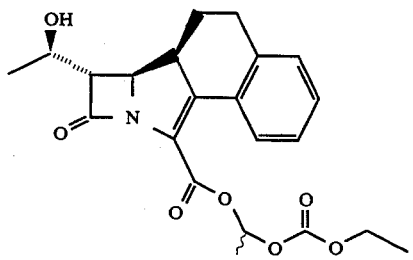

100 mg (0.30 mmol) of potassium (1S,5R,6S)-6-[(1R)-1-hydroxyethyl]-(1,2,3,4-tetrahydronaphtho)[2,1-a]carbapen-2-em-3-carboxylate (Example 1) were dissolved in 2.5 ml of anhydrous DMF and 145 mg (0.59 mmol) of 1-(ethoxycarbonyloxy)ethyl iodide were added at 0° C. After 30 min, the reaction mixture was taken up in 10 ml of water and extracted twice with 20 ml of ethyl acetate each time. The organic phases were dried over magnesium sulfate and concentrated in vacuo, and the residue was chromatographed on ®LiChroprep RP 18 ( eluent: water/acetonitrile gradient). Yield: 60 mg ( 49% ). —$^1$H-NMR (200 MHz, DMSO): δ=1.17 (d, 3H, CH—CH$_3$); 1.24 (t, 3H, OCH$_2$—CH$_3$); 1.47 (d, 3H, O$_2$CH—CH$_3$); 1.75–2.12 (m, 2H, CH—CH$_2$—CH$_2$); 3.02 (mc, 2H, CH—CH$_2$CH$_2$); 3.18–3.33 (m, 1H, H-6); 3.40 (mc, 1H, CH—CH$_2$—CH$_2$); 4.03 (mc, 1H, H-5); 5.12 (d, 2H, OCH$_2$—CH$_3$); 4.30 and 4.35 (2×dd, 1H, H-5); 5.12 (d, 1H, OH); 6.93 (mc, 1H; OCH(CH$_3$)O; 7.04–7.34 and 7.48–7.70 (2×m, 4H, aromatic H).

EXAMPLE 28

1-(Isobutoxycarbonyloxy)ethyl (1S,5R,6S)-6-[(1R)-1-hydroxyethyl]-(1,2,3,4-tetrahydronaphtho)[2,1-a]carbapen-2-em-3-carboxylate

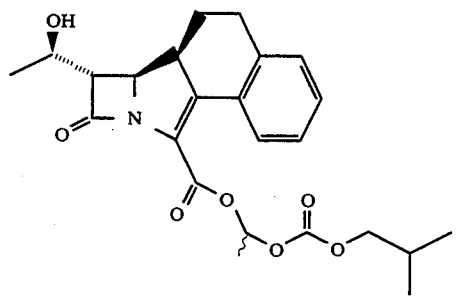

As described in Example 27, 100 mg (0.30 mmol) of potassium salt and 157 mg (0.58 mmol) of 1-(isobutoxycarbonyloxy)ethyl iodide were reacted. After chromatography on ®LiChroprep RP 18, 52 mg (40%) of the prodrug ester were obtained. —$^1$H-NMR (200 MHz, DMSO): δ=0.93 (2×d, 6H, CH(CH$_3$)$_2$); 1.06 (d, 3H, CH—CH$_3$); 1.27–1.41 (m, 4H, OCH(CH$_3$)O and CH—(CH$_3$)$_2$); 1.77–2.10 (m, 2H, CH—CH$_2$CH$_2$); 3.02 (mc, 2H, CH—CH$_2$—CH$_2$); 3.20–3.32 (m, 1H, H-6); 3.36–3.45 (mc, 1H, CH—CH$_2$—CH$_2$); 3.80–4.08 (m, 3H, CH—CH$_3$ and OCH$_3$—CH); 4.30 and 4.36 (2×dd, 1H, H-5); 5.08 and 5.13 (2×d, 1H, OH); 6.82 (mc, 1H, OCH(CH$_3$)O; 7.04–7.33 (m, 3H, aromatic H); 7.60 (d, 1H, aromatic H).

EXAMPLE 29

1-(sec-Butoxycarbonyloxy)ethyl(1S,5R,6S)-6-[(1R)-1-hydroxyethyl]-( 1,2,3,4-tetrahydronaphtho)[2,1-a]carbapen-2-em-3-carboxylate

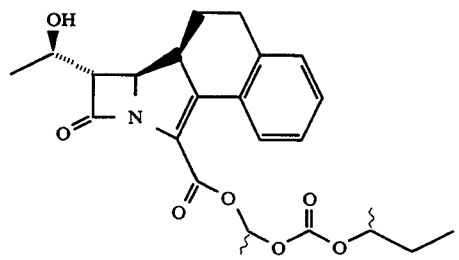

Analogously to Example 27, 100 mg (0.30 mmol) of potassium salt were reacted at 0° C. with 157 mg (0.58 mmol) of 1- (sec-butoxycarbonyloxy)ethyl iodide. After purification on ®LiChroprep RP 18, the product could be obtained as an oil. Yield: 72 mg (55%). —$^1$H-NMR (200 MHz, DMSO): δ=0.94 (t, 3H, CH$_2$—CH$_3$); 1.10–1.28 (m, 6H, CH—CH$_3$ and CH(CH$_3$ )CH$_2$); 1.47 (d, 3H, OCH(CH$_3$)O); 1.58 (mc, 2H, CH$_2$—CH$_3$); 1.86–2.10 (m, 2H, CH—CH$_2$—CH$_2$); 3.02 (mc, 2H, CH—CH$_3$); 1.86–2.10 (m, 2H, CH—CH$_2$—CH$_2$); 3.02 (mc, 2H, CH—CH$_2$—CH$_2$); 3.19–3.30 (m, 1H, H-6); 3.40 (mc, 1H, CH—CH$_2$—CH$_2$); 4.03 (mc, 1H, CH—CH$_3$); 4.27 and 4.35 (2×dd, 1H, H-5); 4.65 (mc, 1H, CH(CH$_3$)CH$_2$); 5.08 and 5.12 (2×d, 1H, OH); 6.38

(mc, 1H, OCH(CH3)O); 7.07–7.32 (m, 3H, aromatic H); 7.60 (d, 1H, aromatic H).

EXAMPLE 30

1-(Butoxycarbonyloxy)ethyl (1S, 5R, 6S)-6-[(1R)-1-hydroxyethyl]-(1,2,3,4-tetrahydronaphtho)[2,1-a]carbapen-2-em-3-carboxylate

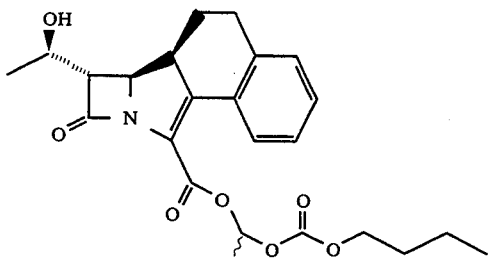

As described in Example 27, 100 mg (0.30 mmol) of potassium salt were reacted with 157 mg (0.58 mmol) of 1-(butoxycarbonyloxy)ethyl iodide. After chromatography on ®LiChroprep RP 18, 44 mg (34%) of product were obtained. —$^1$H-NMR (200 MHz, DMSO): δ=0.90 (t, 3H, CH₂—CH₃); 1.15 (d, 3H, CH—CH₃); 1.20–1.66 (m, 7H, OCH(C₃)O and CH₂—CH₂—CH₃); 1.75–2.13 (m, 2H, CH—C₂—CH₂); 3.03 (mc, 2H, CH—CH₂—CH₂); 3.23–3.42 (m, 2H, H-6 and CH—CH₂—CH₂); 4.02 (mc, 1H, CH—CH₃); 4.15 (t, 2H, OCH₂); 4.28 and 4.33 (2×dd, 1H, H-5); 5.08 and 5.11 (2×s, 1H, OH); 6.83 (mc, 1H, OCH(CH₃)O); 7.07–7.34 (m, 3H, aromatic H); 7.60 (d, 1H, aromatic H).

EXAMPLE 31

Potassium (1S,5R,6S)-6-[(1R)-1-hydroxyethyl]-(6-methoxy-1,2,3,4-tetrahydronaphtho)[2,1-a]carbapen-2-em-3-carboxylate

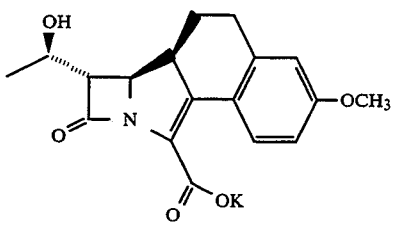

Step 1

(3S ,4R)-3-[(1R)-1-tert-Butyldimethylsilyloxyethyl]-4-[(2R)-6-methoxy-1-oxo-1,2,3,4-tetrahydronaphth-1-yl]-azetidin-2-one Analogously to step 1 in Example 16, 50 g (284 mmol) of 6-methoxytetralone were reacted with 71 g (247 mmol) of 4-acetoxy-3[(1R)-1-tert-butyldimethylsilyloxyethyl]-azetidin-2-one. After chromatography on silica gel (eluent: toluene/ethyl acetate=2:1) and subsequent crystallization from n-heptane, 24.5 g (25%) of the β-isomer were isolated. —$^1$H-NMR (270 MHz, CDCl₃): δ=0.09 (s, 6H, SiCH₃); 0.89 (s, 9H, SiC(CH₃)₃); 1.27 (d, 3H, CH—CH₃); 1.95–2.06 and 2.20–2.33 (2×m, 2H, CH—CH₂—CH₂); 2.69 (mc, 1H, CH—CH₂—CH₂); 3.01–3.12 (m, 3H, CH—C₂—C₂ and H-3); 3.87 (s, 3H, OCH₃); 4.26 (mc, 1H, CH—CH₃); 4.45 (dd, 1H, H-4); 5.72 (bs, 1H, NH); 6.71 (d, 1H, aromatic H); 6.84 (mc, 1H, aromatic H); 7.99 (d, 1H, aromatic H).

Step 2

Allyl [(3S,4R)-3-[(1R)-1-tert-butyldimethylsilyloxyethyl]-4-[(2R)-6-methoxy-1-oxo-1,2,3,4-tetrahydronaphth-2-yl]-2-oxoazetidin-1-yl]-2-oxoacetate.

Analogously to step 2 in Example 1, 2.4 g (5.95 mmol) of the azetidinone were reacted with allyl oxalyl chloride. After chromatography on silica gel (eluent: petroleum ether/ethyl acetate=4:1), 2.4 g (78%) of the product were obtained as a pale yellow solid. —$^1$NMR (CDCl₃, 200 MHz): δ=0.07 and 0.08 (2×s, 6H, SiCB₃); 0.84 (s, 9H, Si(CH₃)₃); 1.18 (d, 3H, CH—CH₃); 1.90–2.32 (m, 2H, CH—CH₂—CH₂); 3.02–3.23 (m, 3H, CH—CH₂—CH₂); 3.34 (dd, 1H, H-3); 3.85 (s, 3H, OCH₃); 4.35 (mc, 1H, CH—CH₃); 4.65 (dd, 1H, H-4); 4.80 (mc, 2H, CH₂—CH=CH₂); 5.36 (mc, 2H,, CH₂—CH=CH₂); 5.97 (mc, 1H, CH₂—CH=CH₂); 6.70 (d, 1H, aromatic H); 6.94 (mc, 1H, aromatic H); 8.00 (d, 1H, aromatic H).

Step 3

Allyl (1S,5R,6S)-6-[(1R)-tert-butyldimethylsilyloxyethyl]-(6-methoxy-1,2,3,4-tetrahydronaphtho)[2,1-a]carbapen-2-em-3-carboxylate.

As described in step 3 of Example 1, 2.4 g (4.6 mmol) of allyl ester were cyclized in anhydrous mesitylene. After chromatography on silica gel (eluent: toluene/ethyl acetate=30:1), 750 mg (33%) of product were isolated. —$^1$H-NMR (200 MHz, CDCl₃): δ=0.07 (s, 6H, SiCH₃); 0.90 (s, 9H, Si(CH₃)₃); 1.27 (d, 3H, CH—CH₃); 1.80–2.14 (m, 2H, CH—CH₂—CH₂); 3.03 (mc, 2H, CH—CH₂—CH₂); 3.10 (mc, 1H, CH—CH₂—CH₂); 3.25 (dd, 1H, H-6); 3.80 (s, 3H, OCH₃); 4.15–4.34 (m, 2H, CH—CH₃ and H-5); 4.78 (mc, 2H, CH₂—CH=CH₂); 5.34 (mc, 2H, CH₂—CH=CH₂); 5.97 (mc, 1H, CH₂—CH=CH₂); 6.60–6.77 (m, 2H, aromatic H); 7.83 (d, 1H, aromatic H).

Step 4

Allyl (1S,5R,6S)-6-[(1R)-1-hydroxyethyl]-(6-methoxy-1,2,3,4-tetrahydronaphtho)[2,1-a]carbapen-2-em-3-carboxylate.

Analogously to step 4 in Example 1, the hydroxyethyl compound was prepared from 500 mg (1.03 mmol) of silyl ether. Yield: 130 mg (34%). —$^1$H-NMR (200 MHz, DMSO): δ=1.16 (d, 3H, CH—CH₃); 1.72–2.08 (m, 2H, CH—CH₂—CH₂); 2.98 (mc, 2H, CH—CH₂—CH₂); 3.09–3.27 (m, 1H, CH—CH₂—CH₂); 3.34 (d, 1H, H-6); 3.75 (s, 3H, OCH₃); 4.00 (mc, 1H, CH—CH₃); 4.28 (dd, 1H, H-5); 4.69 (mc, 2H, CH₂—CH=CH₂); 5.07 (d, 1H, OH); 5.19–5.43 (mc, 2H, CH₂—CH=CH₂); 5.93 (mc, 1H, CH₂—CH=CH₂); 6.63–6.76 (m, 2H, aromatic H); 7.60 (d, 1H, aromatic H).

Step 5

Potassium (1S, 5R, 6S)-6-[(1R)-1-hydroxyethyl]-(6-methoxy-1,2,3,4-tetrahydronaphtho)[2,1-a]carbapen-2-em-3-carboxylate.

Analogously to step 5 in Example 1, 114 mg (0.308 mmol) of allyl ester were reacted. After chromatography on ®LiChroprep RP 18 (eluent: water, acetonitrile gradient 0–15%) and lyophilization, 48 mg (42%) of the potassium salt were obtained. —$^1$H-NMR (200 MHz, DMSO): δ=1.15 (d, 3H, CH—CH₃); 1.62 and 1.94 (2×mc, 2H, CH—CH₂—CH₂); 2.75–3.00 (m, 3H, CH—CH₂—CH₂); 3.16 (dd, 1H, H-6); 3.69 (s, 3H, OCH₃); 3.95 (mc, 1H, CH—CH₃); 4.07 (dd, 1H, H-5);

4.96 (bs, 1H, OH); 6.52–6.73 (m, 2H, aromatic H); 7.68 (d, 1H, aromatic H).

What is claimed is:

1. A β-lactam antibiotic of the formula I, or a pharmaceutically tolerable salt thereof

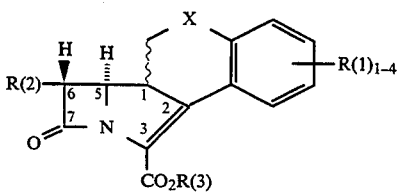

in which:

X is: $(CH_2)_n$ where n=0 or 2;

CR(a)R(b), where R(a) and R(b) are selected independently of one another from: H;

$(C_1-C_6)$-alkyl; aryl selected from phenyl and naphthyl, which aryl is unsubstituted or substituted by $(C_1-C_4)$-alkyl, F, Cl, Br, $O(C_1-C_4)$-alkyl, OH, $OCO(C_1-C_4)$-alkyl, $NH_2$, $NH(C_1-C_4)$-alkyl, $OCOC_6H_5$ or $NHC_6H_5$; heteroaryl selected from a 5- to 6-membered ring which has 1 to 4N, O or S atoms and which is unsubstituted or substituted by $(C_1-C_4)$-alkyl, F, Cl, Br, $O(C_1-C_4)$-alkyl, OH, $OCO(C_1-C_4)$-alkyl, $NH_2$, $NH(C_1-C_4)$-alkyl, $OCOC_6H_5$ or $NHC_6H_5$;

O;

$SO_n$ where n=0, 1 or 2;

NR(c), where R(c) is selected from H, $(C_1-C_6)$-alkyl, aryl, $CO(C_1-C_6)$-alkyl, CO-aryl, CO-heteroaryl, $(C_1-C_6$-alkoxycarbonyl, $(C_1-C_6)$-alkylsulfonyl and arylsulfonyl;

R(1) is: up to four substituents which are identical or different, selected from H and $(C_1-C_6)$-alkyl, a substituent selected from aryl, heteroaryl, OH, SH, $SO_n(C_1-C_6)$-alkyl, where n=0, 1 or 2, NR(b)R(c), where R(b) and R(c) are as defined above, CN, $NO_2$ and C(R(a))=NOR(b), where R(a) and R(b) are as defined above, up to two substituents selected from $CF_3$, F, Cl, Br, I, $O(C_1-C_6)$-alkyl, $OCO(C_1-C_6)$-alkyl, OCONR(d)R(e), where R(d) and R(e) are selected independently of one another from: hydrogen and $(C_1-C_6)$-alkyl, or NR(d)R(e) corresponds to a 5- or 6-membered ring system, $SO_2NR(d)R(e)$, where R(d) and R(e) are as defined above, $CO(C_1-C_6$-alkyl, CO-aryl, $CO_2H$, $CO_2(C_1-C_6)$-alkyl, CONR(d)R(e), where R(d) and R(e) are as defined above, $CH_2R(f)$, where R(f) is selected from: hydroxyl, $(C_1-C_6)$-alkoxy, acyloxy, aryloxy, heteroaryloxy, $(C_1-C_6)$-alkylthio, arylthio, heteroarylthio and the sulfinyl and sulfonyl compounds which can be derived therefrom, and NR(b)R(c), where R(b) and R(c) are as defined above, or which NR(b)R(c) is part of a cyclic or heterocyclic system; $NHCO(C_1-C_6)$-alkyl; $NHCOC_6H_5$ and NHCO-naphthyl;

R(2) is: $NH_2$; NHR(a)R(b); $NHCO(C_1-C_4)$-alkyl;

R(3) is: H, $(C_1-C_3)$-alkyl-$OCO(C_1-C_6)$-alkyl, $(C_1-C_3)$-alkyl-$OCO_2(C_1-C_6)$-alkyl or (5-methyl-1-3-dioxolen-2-on-4-yl)methyl, and in which compounds are excluded in which R(1) is hydrogen four times.

2. A compound of the formula I as claimed in claim 1, wherein the stereochemistry is 5R,6S.

3. A method for the treatment of microbial infections, which comprises providing an effective amount of a compound of the formula I as claimed in claim 1 with pharmaceutically customary additives and administering to the host to be treated.

4. A pharmaceutical composition for the treatment of a microbial infection, which contains an effective amount of a compound of the formula I as claimed in claim 1.

5. A method for the treatment of microbial infections which comprises administering to a host in need of said treatment an effective amount of a compound of the formula I as claimed in claim 1.

* * * * *

UNITED STATES PATENT AND TRADEMARK OFFICE
CERTIFICATE OF CORRECTION

PATENT NO. : 5,405,844
DATED : April 11, 1995
INVENTOR(S) : Uwe GERLACH et al

It is certified that error appears in the above-indentified patent and that said Letters Patent is hereby corrected as shown below:

Claim 1, Column 50, Line 19, should read:  --R(2) is: $NH_2$; NHR(a)R(b); $NHCO(C_1-C_4)$-alkyl; $NHCOC_6H_5$ or NHCO-naphthyl;--

Signed and Sealed this

Fifth Day of March, 1996

BRUCE LEHMAN

Attest:

Attesting Officer        Commissioner of Patents and Trademarks